United States Patent
Faull et al.

(10) Patent No.: US 6,833,387 B1
(45) Date of Patent: Dec. 21, 2004

(54) CHEMICAL COMPOUNDS

(75) Inventors: Alan W. Faull, Macclesfield (GB); Jason Kettle, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/889,516

(22) PCT Filed: Jan. 31, 2000

(86) PCT No.: PCT/GB00/00284

§ 371 (c)(1),
(2), (4) Date: Oct. 2, 2001

(87) PCT Pub. No.: WO00/46199

PCT Pub. Date: Aug. 10, 2000

(30) Foreign Application Priority Data

Feb. 5, 1999 (GB) ............................................. 9902455

(51) Int. Cl.[7] ....................... A61K 31/38; C07D 209/36
(52) U.S. Cl. ...................................... 514/484; 548/443
(58) Field of Search ........................... 548/484; 514/443

(56) References Cited

U.S. PATENT DOCUMENTS

| | | |
|---|---|---|
| 3,557,142 A | 1/1971 | Bell |
| 3,776,923 A | 12/1973 | Remers et al. |
| 3,997,557 A | 12/1976 | Helsley et al. |
| 4,529,724 A | 7/1985 | Ho |
| 4,608,384 A | 8/1986 | Wierzbicki et al. |
| 4,721,725 A | 1/1988 | Biller et al. |
| 4,751,231 A | 6/1988 | Halczenko et al. |
| 4,965,369 A | 10/1990 | Maetzel et al. |
| 5,081,145 A | 1/1992 | Guindon et al. |
| 5,190,968 A | 3/1993 | Gillard et al. |
| 5,254,563 A | 10/1993 | Huth et al. |
| 5,260,322 A | 11/1993 | Nakaisima et al. |
| 5,272,145 A | 12/1993 | Prasit et al. |
| 5,273,980 A | 12/1993 | Frenette et al. |
| 5,288,743 A | 2/1994 | Brooks et al. |
| 5,290,798 A | 3/1994 | Gillard et al. |
| 5,308,850 A | 5/1994 | Gillard et al. |
| 5,334,719 A | 8/1994 | Frenette |
| 5,389,650 A | 2/1995 | Frenette et al. |
| 5,399,699 A | 3/1995 | Kolasa et al. |
| 5,401,287 A | 3/1995 | Pecoraro et al. |
| 5,482,960 A | 1/1996 | Berryman et al. |
| 5,604,253 A | 2/1997 | Lau et al. |
| 5,639,780 A | 6/1997 | Lau et al. |
| 5,684,032 A | 11/1997 | Elliott et al. |
| 5,852,046 A | 12/1998 | Lang et al. |
| 5,877,199 A | 3/1999 | Birdsall et al. |
| 5,955,492 A | 9/1999 | Thompson et al. |
| 6,184,235 B1 | 2/2001 | Connor et al. |
| 6,500,853 B1 * | 12/2002 | Seehra et al. ............... 514/415 |

FOREIGN PATENT DOCUMENTS

| | | |
|---|---|---|
| DE | 298 913 A5 | 3/1992 |
| EP | 0 077 209 | 4/1983 |
| EP | 0 186 367 | 7/1986 |
| EP | 0 189 690 | 8/1986 |
| EP | 0 275 667 | 7/1988 |
| EP | 0 419 049 A1 | 3/1991 |
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 639 573 A1 | 2/1995 |
| EP | 0 822 185 | 2/1998 |
| FR | 2 565 981 | 12/1985 |
| JP | 63-284177 | 11/1988 |
| JP | 4-273857 | 9/1992 |
| WO | WO 86/00896 | 2/1986 |
| WO | WO 92/04343 | 3/1992 |
| WO | WO 93/12780 | 7/1993 |
| WO | WO 93/16069 | 8/1993 |
| WO | WO 93/20078 | 10/1993 |
| WO | WO 94/14434 | 7/1994 |
| WO | WO 96/31492 | 10/1996 |
| WO | WO 96/33171 | 10/1996 |
| WO | WO 97/12613 | 4/1997 |

(List continued on next page.)

OTHER PUBLICATIONS

Krutosikova, A. et al. Synthesis and Reactions of Furo[2, 3–b]pyrroles. Molecules 2, 69–79 (1997).

Berman, J.W. et al. Localization of Monocyte Chemoattractant Peptide–1 Expression in the Central Nervous System in Experimental Autoimmune Encephalomyclitis and Trauma in the Rat. *J. Immunol.* 156, 3017–3023 (1996).

Bobosik, V. & Krulosikova, A. Synthesis of N–Phenylsulfonyl Protected Furo[3,2–b]Pyrroles. *Collect. Czech. Chem. Commun.* 59, 499–502 (1994).

(List continued on next page.)

*Primary Examiner*—Joseph K. McKane
*Assistant Examiner*—Binta Robinson
(74) *Attorney, Agent, or Firm*—Ropes & Gray LLP

(57) ABSTRACT

The use of a 3-substituted indole compound of formula (I) or a pharmaceutically acceptable salt, amide or ester thereof; X is $CH_2$ or $SO_2$ and $R^1$, $R^2$, $R^3$, $R^4$, $R^5$, $R^6$ and $R^7$ are certain specified organic moieties, for use in the preparation of a medicament for the inhibition of monocyte chemoattractant protein-1 and/or RANTES induced chemotaxis. Pharmaceutical compositions containing certain compounds of formula (I) and novel compounds of formula (I) are also described and claimed.

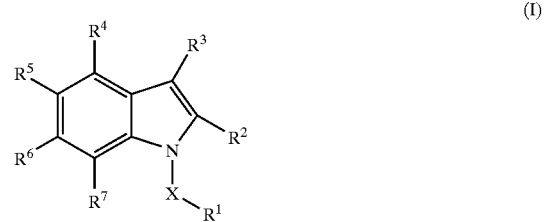

(I)

8 Claims, No Drawings

FOREIGN PATENT DOCUMENTS

| | | |
|---|---|---|
| WO | WO 97/12615 | 4/1997 |
| WO | WO 97/30704 | 8/1997 |
| WO | WO 97/35572 | 10/1997 |
| WO | WO 98/06703 | 2/1998 |
| WO | WO 99/07351 | 2/1999 |
| WO | WO 99/07678 | 2/1999 |
| WO | WO 99/33800 | 7/1999 |

OTHER PUBLICATIONS

Dandarova, M. 13C NMR Spectra of Some Substituted Furo[3,2–b]pyrroles. *Magnetic Resonance Chem.* 28, 830–831 (1990).

Deleuran, M. et al. Localization of monocyte chemotactic and activating factor (MCAF/MCP–1) in psoriasis. *J. Dermatological Sci.* 13, 228–236 (1996).

Grimm, M.C. et al. Enhanced expression and production of moncyte chemoattractant protein–1 in inflammatory bowel disease mucosa. *J. Leukocyte Biol.* 59, 804–812 (Jun. 1996).

Harrison, C.–A. et al. Cyclopenta [b] indoles. Part 2. Model studies towards the tremorgenic mycotoxins. *J. Chem. Soc. Perkin Trans.* 1131–1136 (1995).

Hartman, G.D. & Halczenko, W. The Synthesis of 5–Alkylaminomethylthieno[2,3–b]pyrrole–5–sulfonamides. *Heterocycles* 29, 1943–1949 (1989).

Jones, M.L. et al. Potential Role of Monocyte Chemoattractant Protein 1/JE in Monocyte/Macrophage–Dependent IgA Immune Complex Alveolitis in the Rat. *J. Immunol.* 149, 2147–2154 (Sept. 15, 1992).

Kataoka, K. et al. Homopiperazines as cell migration inhibitors. *Chemical Abstracts,* Columbus Ohio, US 123, 667 (Oct. 2, 1995).

Koch, A.E. et al. Enhanced Production of Monocyte Chemoattractant Protein–1 Rheumatoid Arthritis. *J. Clin. Invest.* 90, 772–779 (Sept. 1992).

Korobchenko, L.V. et al. Synthesis and antiviral activity of pyrrolecarboxylic acids and their derivatives. *Chemical Abstracts* Columbus, Ohio, Access No.: 119:62465 (1999).

Krutosikova, A. & Dandarova, M. Substituted Vinyl Azides in Synthesis of Furo[3,2–b:4,5–b]–Dipyrroles and Pyrrolo [2',3':4,5]Furo[3,2–c]Pyridines. *Heterocycles* 37, 1695–1700 (1994).

Krutosikova, A. & Dandarova, M. Reactions of Methyl 2–Formylfuro[3,2–b]pyrrole–5–carboxylates. *Chem. Papers* 50, 72–76 (1996).

Krutosikova, A. & Hanes, M. Substituted 4–Benzylfuro[3, 2–b]Pyrroles. *Collect. Czech Chem.* 57, 1487–1494 (1992).

Krutosikova, A. et al. Condensed O–, N–Heterocycles by the Transformation of Azidoacrylates. *Chemical Monthly* 123, 807–815 (1992).

Krutosikova, A. et al. Derivatives of Furo[3,2–b]Pyrrole. *Collect. Czech. Chem. Commun.* 59, 473–481 (1994).

Krutosikova, A. et al. Substituted Vinyl Azides in the Synthesis of Condensed Nitrogen Heterocycles. *Chem. Papers* 48, 268–273 (1994).

Krutosikova, A. et al. Synthesis and Reactions of Furo[3, 2–b]Pyrrole Type Aldehydes. *Collect Czech. Chem. Commune.* 58, 2139–2149 (1993).

Y. Yokoyama et al.: "New Synthetic Method for Dehydrotryptophan derivatives. Synthetic Studies on Indole and Related Compounds. XXXIV". Chemical and Pharmaceutical Bulletin, vol. 42, No. 4, 1994, pp. 832–838, XP000887306, p. 834, compound 18d; p. 835, compound 9b.

Y. Murakami et al. : "Direct Regioselective Vinylation of Indoles Using Palladium (II) Chloride ." HETEROCYCLES, vol. 22, No. 7, 1984, pp. 1493–1496, XP000909376 p. 1494, compound 3c; p. 1495, compound 6.

P. Rosenmund et al. : "Decarboxylierungen einiger, 1–Alkyl–2–carboxy–3–indolessigsauren sowie Synthese eines, 5–Thiocyanato–2, 3–dihydroindols." Chemische Berichte, vol. 108, 1975, pp. 3538–3542, XP000909395 p. 3539, compound 2d.

R. Troschutz et al.: "Synthesis of Substituted, 3–Amino–4–Cyano–1–oxo–1,2,5,10–tetrahydroa zepino [3,4–b] indoles." Journal of Heterocyclic Chemistry, vol. 34, 1997, pp. 1431–1440, XP000909451, p. 1439, col. 1, paragraph 4.

\* cited by examiner

CHEMICAL COMPOUNDS

This application is the National Phase of International Application PCT/GB00/00284 filed Jan. 31, 2000 which designated the U.S. and that International Application was published under PCT Article 21(2) in English.

The present invention relates to chemical compounds, to their production as well as to pharmaceutical compositions containing them as well as to their use in therapy, in particular of inflammatory disease.

MCP-1 is a member of the chemokine family of pro-inflammatory cytokines which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, *J. Immunol.*, 149, 2147) and asthma. Other disease areas where MCP-1 is thought to play a part in their pathology are atherosclerosis (e.g. Koch et al., 1992, *J. Clin. Invest.*, 90, 772–779), psoriasis (Deleuran et al., 1996, *J. Dermatological Science*, 13,. 228–236), delayed-type hypersensitivity reactions of the skin, inflammatory bowel disease (Grimm et al., 1996, *J. Leukocyte Biol.*, 59,. 804–812), multiple sclerosis and brain trauma (Berman et al, 1996, *J. Immunol.*, 156,. 3017–3023). An MCP-1 inhibitor may also be useful to treat stroke, reperfusion injury, ischemia, myocardial infarction and transplant rejection.

MCP-1 acts through the MCP-1 receptor (also known as the CCR2 receptor). MCP-2 and MCP-3 may also act, at least in part, through the MCP-1 receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the MCP-1 receptor.

Copending International Patent Application Nos. PCT/GB98/02340 and PCT/GB98/02341 describe and claim groups of compounds based upon the indole ring structure which are inhibitors of MCP-1 and therefore have applications in therapy.

The use of certain indole derivatives as NMDA antagonists is described is U.S. Pat. No. 5,051,442, WO9312780, EP-483881. Other indoles and their use as inhibitors of leukotriene biosynthesis is described in for example. EP-A-275-667.

The applicants have found a particular substitution on the indole ring produces advantageous results when used therapeutically as inhibitors of MCP-1.

According to the present invention there is provided the use of a compound of formula (I)

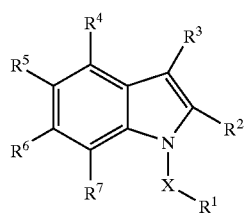

(I)

X is $CH_2$ or $SO_2$
$R^1$ is an optionally substituted aryl or heteroaryl ring;
$R^2$ is carboxy, cyano, —$C(O)CH_2OH$, —$CONHR^8$, —$SO_2NHR^9$, tetrazol-5-yl, $SO_3H$, or a group of formula (VI)

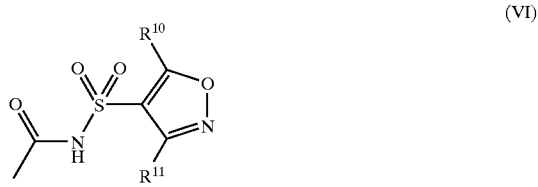

(VI)

where
$R^8$ is selected from hydrogen, alkyl, aryl, cyano, hydroxy, —$SO_2R^{12}$ where $R^{12}$ is alkyl, aryl, heteroaryl, or haloalkyl, or $R^8$ is a group —$(CHR^{13})_r$—COOH where r is an integer of 1–3 and each $R^{13}$ group is independently selected from hydrogen or alkyl; $R^9$ is hydrogen, alkyl, optionally substituted aryl such as optionally substituted phenyl or optionally subtituted heteroaryl such as 5 or 6 membered heteroaryl groups, or a group $COR^{14}$ where $R^{14}$ is alkyl, aryl, heteroaryl or haloalkyl; $R^{10}$ and $R^{11}$ are independently selected from hydrogen or alkyl, particularly $C_{1-4}$ alkyl; $R^3$ is a group $OR^{15}$, $S(O)_qR^{15}$, $NHCOR^{16}$, $NHSO_2R^{16}$, $(CH_2)_sCOOH$, $(CH_2)_1CONR^{17}R^{18}$, $NR^{17}R^{18}$, $SO_2NR^{17}R^{18}$ or optionally substituted alkenyl, where q is 0, 1 or 2, s is 0 or an integer of from 1 to 4, t is 0 or an integer of from 1 to 4, $R^{15}$ is a substituted alkyl or cycloalkyl group or an optionally substituted heteroaryl group, $R^{16}$ is optionally substituted alkyl, optionally substituted aryl or optionally substituted heteroaryl and $R^{17}$ and $R^{18}$ are independently selected from hydrogen, optionally substituted alkyl, optionally substituted aryl and optionally substituted heteroaryl, with the proviso that at least one of $R^{17}$ or $R^{18}$ is other than hydrogen, or $R^{16}$ and $R^{17}$ together with the nitrogen atom to which they are attached form an optionally substituted heterocyclic ring which optionally contains further heteroatoms; and $R^4$, $R^5$, $R^6$ and $R^7$ are independently selected from hydrogen, a functional group or an optionally substituted hydrocarbyl groups or optionally substituted heterocyclic groups: for use in the preparation of a medicament for the inhibition of monocyte chemoattractant protein-1 and/or RANTES induced chemotaxis.

Pharmaceutically acceptable salts, esters and amides of compounds of formula (I) may also be used in this way.

In particular in the above formula s is an integer of from 1 to 4.

Suitably $R^4$ is other than a group $OR^{18'}$, $S(O)_mR^{18'}$, $NR^{19}R^{20}$, $C(O)NR^{19}R^{20}$, $NHCOR^{18}$, $NHSO_2R^{18}$ or $OCONR^{19}R^{20}$ or an alkyl group substituted by $OR^{18}$, $S(O)_m R^{18}$, $NR^{19}R^{20}$ where $R^{18}$, $R^{19}$, $R^{20}$ and m are as defined hereinafter and $R^{18'}$ is a substituted hydrogen-containing alkyl group.

Compounds of formula (I) are inhibitors of monocyte chemoattractant protein-1. In addition, they appear to inhibit RANTES induced chemotaxis. RANTES is another chemokine from the same family as MCP-1, with a similar biological profile, but acting though the CCR1 receptor. As a result, these compounds can be used to treat disease mediated by these agents, in particular inflammatory disease. Thus the invention further provides a compound of formula (I) for use in preparation of a medicament for the treatment of inflammatory disease.

In this specification the term 'alkyl' when used either alone or as a suffix includes straight chained, branched structures. These groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The term "functional group" refers to reactive substituents. They may comprise electron-donating or electron-withdrawing. Examples of such groups include halo, cyano, nitro, $C(O)_mR^{18}$, $OR^{18}$, $S(O)_mR^{18}$, $NR^{19}R^{20}$, $C(O)NR^{19}R^{20}$, $OC(O)NR^{19}R^{20}$, $-NR^{19}C(O)_nR^{18}$, $-NR^{18}CONR^{19}R^{20}$, $-N=CR^{18}R^{19}$, $S(O)_nNR^{19}R^{20}$ or $-NR^{19}S(O)_nR^{18}$ where $R^{18}$, $R^{19}$ and $R^{20}$ are independently selected from hydrogen or optionally substituted hydrocarbyl, or $R^{19}$ and $R^{20}$ together with the atom to which they are attached, form an optionally substituted heterocyclyl ring as defined above which optionally contains further heteroatoms such as $S(O)_n$, oxygen and nitrogen, n is an integer of 1 or 2, m is 0 or an integer of 1–3.

Suitable optional substituents for hydrocarbyl groups $R^{18}$, $R^{19}$ and $R^{20}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_m$ where m is as defined above.

Where $R^{19}$ and $R^{20}$ together form a heterocyclic group, this may be optionally substituted by hydrocarbyl such as alkyl as well as those substituents listed above for hydrocarbyl groups $R^{18}$, $R^{19}$ and $R^{20}$.

Suitable substituents for hydrocarbyl or heterocylic groups $R^5$, $R^6$ and $R^7$ include those listed above for $R^{18}$, $R^{19}$ and $R^{20}$.

Suitably $R^1$ is an optionally substituted phenyl, pyridyl, naphthyl, furyl or thienyl ring, and in particular is a substituted phenyl or pyridyl ring.

Suitable optional substitutents for $R^1$ in formula (I) include alkyl, alkenyl, alkynyl, halo, haloalkyl including perhaloalkyl such as trifluoromethyl, mercapto, alkoxy, haloalkoxy, alkenyloxy, alkynyloxy, hydroxyalkoxy, alkoxyalkoxy, alkanoyl, alkanoyloxy, cyano, nitro, amino, mono- or di-alkyl amino, oximino, sulphonamido, carbamoyl, mono or dialkylcarbamoyl or $S(O)_mR^{21}$ where m is as defined above and $R^{21}$ is hydrocarbyl.

Suitably $R^4$ is selected from hydrogen, hydroxy, halo, alkoxy, aryloxy or an optionally substituted hydrocarbyl group or optionally substituted heterocyclic group.

Particular examples of substituents $R^4$ include hydrogen, hydroxy, halo, optionally substituted alkyl such as aralkyl, carboxyalkyl or the amide derivative thereof, alkoxy, or Most preferably $R^4$ is hydrogen.

Particular examples of substituents $R^5$, $R^6$ and $R^7$ include hydrogen, hydroxy, halo, optionally substituted alkyl such as aralkyl, carboxyalkyl or the amide derivative thereof; alkoxy; aryloxy; aralkyloxy; or an amino group which is optionally substituted with alkyl, aryl or aralkyl. A specific functional group which is suitable for $R^5$, $R^6$ and/or $R^7$ is a group of sub-formula (IV).

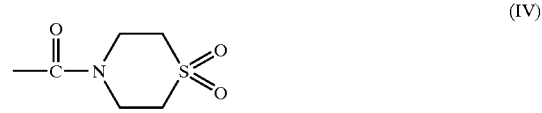

(IV)

Particular examples of groups $R^5$, $R^6$ and $R^7$ are hydrogen, hydroxy, halo or alkoxy. In particular $R^6$ and $R^7$ are hydrogen. $R^5$ may be hydrogen but in addition are suitably a small subsitutent such as hydroxy, halo or methoxy.

Particular substituents for $R^1$ include trifluoromethyl, $C_{1-4}$alkyl, halo, trifluoromethoxy, $C_{1-4}$alkoxy, $C_{1-4}$alkanoyl, $C_{1-4}$alkanoyloxy, nitro, carbamoyl. $C_{1-4}$alkoxycarbonyl, $C_{1-4}$alkylsulphanyl, $C_{1-4}$alkylsulphinyl, $C_{1-4}$alkylsulphonyl, sulphonamido, carbamoyl$C_{1-4}$alkyl, N-($C_{1-4}$alkyl)carbamoyl$C_{1-4}$alkyl, N-($C_{1-4}$alkyl)$_2$carbamoyl-$C_{1-4}$alkyl, hydroxy$C_{1-4}$alkyl or $C_{1-4}$alkoxy$C_{1-4}$alkyl.

Additionally or alternatively, two such substituents together may form a divalent radical of the formula —O(CH$_2$)$_{1-4}$O— attached to adjacent carbon atoms on the $R^1$ ring.

Preferred substitutents for $R^1$ are one or more non-polar substitutents such as halo.

In particular, $R^1$ is substituted by one or more halo groups, in particular chlorine. A particular example of an $R^1$ group is 3,4-dichlorophenyl, 3-fluoro-4-chlorophenyl, 3-chloro-4-fluorophenyl or 2,3-dichloropyrid-5-yl.

Examples of groups $R^2$ include carboxy; cyano; tetrazol-5-yl; SO$_3$H; —CONHR$^8$ where $R^8$ is selected from cyano, hydroxy, —SO$_2$R$^{12}$ where $R^{12}$ is alkyl such as $C_{1-4}$ alkyl, aryl such as phenyl, heteroaryl or trifluoromethyl, or $R^8$ is a group —(CHR$^{10}$)$_r$—COOH where r is an integer of 1–3 and each $R^{10}$ group is independently selected from hydrogen or alkyl such as $C_{1-4}$ alkyl; or $R^2$ is a group —SO$_2$NHR$^9$ where $R^9$ is an optionally substituted phenyl or an optionally substituted 5 or 6 membered heteroaryl group, or a group COR$^{14}$ where $R^{14}$ is alkyl such as $C_{1-4}$ alkyl, aryl such as phenyl, heteroaryl or trifluoromethyl, or $R^2$ is a group of formula (VI)

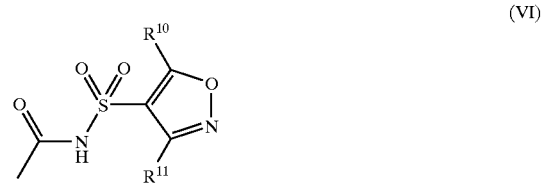

(VI)

where $R^{10}$ and $R^{11}$ are independently selected from hydrogen or alkyl, particularly $C_{1-4}$ alkyl.

Preferably $R^2$ is carboxy or a pharmaceutically acceptable salt or ester thereof.

Particular groups $R^3$ include $OR^{15}$, $S(O)_qR^{15}$, $NHCOR^{16}$, $NHSO_2R^{16}$, $SO_2NR^{17}R^{18}$ where q, $R^{15}$, $R^{16}$, $R^{17}$ and $R^{18}$ are as defined above.

Suitable optional substitutents for the group $R^{15}$, $R^{16}$, $R^{17}$ and $R^{18}$ as they appear in the definition of $R^3$, or alkenyl groups $R^3$ as defined above include functional groups as hereinbefore defined, as well as aryl or heteroaryl groups, either of which may themselves be substituted by one or more functional groups.

Particular examples of substituents for groups $R^{15}$, $R^{16}$, $R^{17}$ and $R^{18}$ include one or more groups selected from halo such as chloro, hydroxy, cyano, amino, mono- or di-alkylamino, $C_{1-4}$ alkoxy, carboxy, sulphonamido, $CONH_2$, morpholino, pyridyl, pyrimidinyl, phenyl optionally substituted by halo such as chloro, carboxy, hydroxy, alkoxy such as methoxy, carbamoyl, acyl such as acetyl, or hydroxyalkyl where the alkyl group suitably includes at least two carbon atoms, such as hydroxyethyl.

Where $R^{15}$, $R^{16}$, $R^{17}$ and $R^{18}$ is a heteroaryl group, or where $R^{17}$ and $R^{18}$ together form an optionally substituted heterocyclic ring, these may be substituted by functional groups, or by alkyl groups such as methyl or ethyl, or alkenyl or alkynyl groups any of which may be subsituted, for example with hydroxy.

A preferred group for $R^3$ is a group $OR^{15}$ straight or branched chain alkyl group which carries at least one hydroxy group, for example or 2 hydroxy groups. Other substituents, as defined above, may be provided on the alkyl chain.

Preferably $R^3$ is a group of formula —$O(CH_2)_a[(CHOH)(CH_2)_b]_dCH_2OH$ where a is 0 or an integer of from 1 to 4, b is 0 or an integer of from 1 to 3, and d is 0, or 1.

Examples of such $R^3$ include $OCH_2CHOHCH_2OH$ and $OCH_2CH_2OH$.

X is $CH_2$ or $SO_2$ and is preferably $CH_2$.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include alkyl esters, such as $C_{1-6}$ alkyl esters for example, ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically acceptable esters of compounds of formula (I) are in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Esters which are not in vivo hydrolysable are useful as intermediates in the production of the compounds of formula (I) and therefore these form a further aspect of the invention.

Thus examples of compounds of formula (I) include the following:

TABLE 1

| Compd No. | $R^3$ | $R^4$ | $R^5$ | $R^6$ | $R^a$ | $R^b$ |
|---|---|---|---|---|---|---|
| 1 | (N-methyl-N-(3-chlorobenzoyl)amino) | H | H | H | Cl | Cl |

TABLE 1-continued

[Structure: indole with R3, R4, R5, R6 substituents on ring, N-benzyl group with Ra, Rb substituents, and 2-COOH]

| Compd No. | R³ | R⁴ | R⁵ | R⁶ | Rᵃ | Rᵇ |
|---|---|---|---|---|---|---|
| 2 | —NHS(O)₂CH₃ | H | H | H | Cl | Cl |
| 3 | methylsulfonyl-morpholine | H | H | H | Cl | Cl |
| 4 | methylsulfonyl-thiomorpholine-1,1-dioxide | H | H | H | Cl | Cl |
| 5 | —SCH₂(C₆H₅) | H | H | H | Cl | Cl |
| 6 | methylsulfonyl-4-methylpiperazine | H | H | H | Cl | Cl |
| 7 | S(O)₂N(CH₂)₂NH₂ | H | H | H | Cl | Cl |
| 8 | 3,5-dimethylisoxazole-4-sulfonyl-N-methyl | H | H | H | Cl | Cl |
| 9 | 2-acetamido-thiazole-5-sulfonyl-N-methyl | H | H | H | Cl | Cl |
| 10 | 1-methylimidazole-4-sulfonyl-N-methyl | H | H | H | Cl | Cl |
| 11 | NHS(O)₂CH₂COOH | H | H | H | Cl | Cl |

TABLE 1-continued
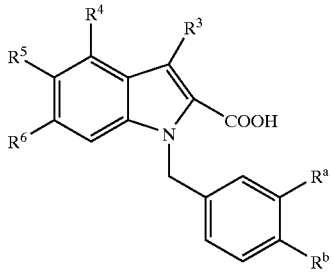
| Compd No. | R³ | R⁴ | R⁵ | R⁶ | Rᵃ | Rᵇ |
|---|---|---|---|---|---|---|
| 12 | 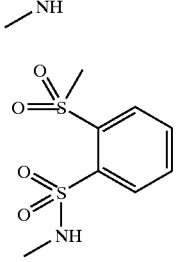 | H | H | H | Cl | Cl |
| 13 | 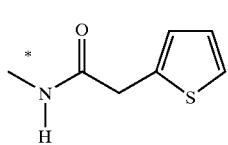 | H | H | H | Cl | Cl |
| 14 | NHC(O)CH₂COOH | H | H | H | Cl | Cl |
| 15 | NHC(O)CH₂CH₂OCH₃ | H | H | H | Cl | Cl |
| 16 | 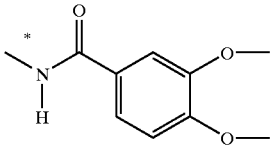 | H | H | H | Cl | Cl |
| 17 | NHC(O)CH(OH)CH₃ | H | H | H | Cl | Cl |
| 18 | 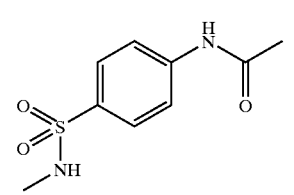 | H | H | H | Cl | Cl |
| 19 | 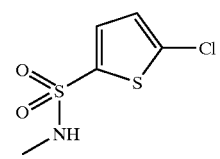 | H | H | H | Cl | Cl |
| 20 |  | H | H | H | Cl | Cl |

TABLE 1-continued
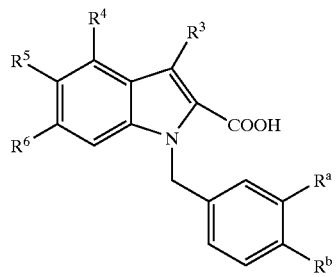
| Compd No. | R³ | R⁴ | R⁵ | R⁶ | Rᵃ | Rᵇ |
|---|---|---|---|---|---|---|
| 21 | 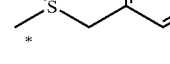 | H | H | H | Cl | Cl |
| 22 | 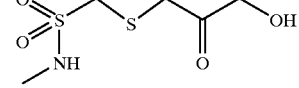 | H | H | H | Cl | Cl |
| 23 | OCH₂CH₂OH | H | H | H | Cl | Cl |
| 24 | SCH₂C(O)₂H | H | H | H | Cl | Cl |
| 25 | 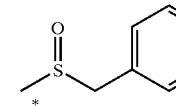 | H | H | H | Cl | Cl |
| 26 | 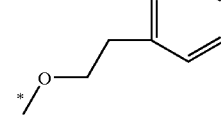 | H | H | H | Cl | Cl |
| 27 | OCH₂COOH | H | H | H | Cl | Cl |
| 28 | CH₂COOH | H | H | H | Cl | Cl |
| 29 | S(O₂)NH(CH₂)₂OH | H | H | H | Cl | Cl |
| 30 | S(O₂)N((CH₂)₂OH)₂ | H | H | H | Cl | Cl |
| 31 | 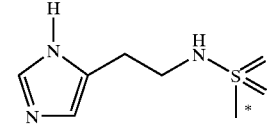 | H | H | H | Cl | Cl |
| 32 | 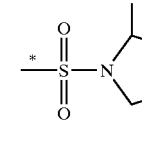 | H | H | H | Cl | Cl |
| 33 | 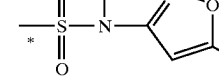 | H | H | H | Cl | Cl |

TABLE 1-continued

| Compd No. | R³ | R⁴ | R⁵ | R⁶ | Rᵃ | Rᵇ |
|---|---|---|---|---|---|---|
| 34 | (furan-3-yl-CH₂-N(CH₃)-SO₂-CH₃, attached via methyl*) | H | H | H | Cl | Cl |
| 35 | HO-CH₂CH₂-N(piperazine)N-S(O)₂-* | H | H | H | Cl | Cl |
| 36 | morpholine-N-CH₂CH₂-NH-S(O)₂-* | H | H | H | Cl | Cl |
| 37 | pyridin-2-yl-CH₂-NH-S(O)₂-* | H | H | H | Cl | Cl |
| 38 | S(O)₂NHCH₂CH(OCH₃)₂ | H | H | H | Cl | Cl |
| 39 | S(O)₂NHCH₂C≡CH | H | H | H | Cl | Cl |
| 40 | S(O)₂N((CH₂)₂OCH₃)₂ | H | H | H | Cl | Cl |
| 41 | 4-acetylpiperidin-N-S(O)₂-* | H | H | H | Cl | Cl |
| 42 | (2-hydroxyphenyl)-CH₂-N(CH₃)-S(O)₂-* | H | H | H | Cl | Cl |
| 43 | *-S(O)₂-N(3-hydroxypyrrolidin-1-yl) | H | H | H | Cl | Cl |
| 44 | *-S(O)₂-CH₃-NH-CH₂-(1H-benzimidazol-2-yl) | H | H | H | Cl | Cl |

TABLE 1-continued

| Compd No. | R³ | R⁴ | R⁵ | R⁶ | Rᵃ | Rᵇ |
|---|---|---|---|---|---|---|
| 45 | isoxazol-3-yl-NH-S(O)₂-CH₃ (methanesulfonamide linked via isoxazole) | H | H | H | Cl | Cl |
| 46 | 1H-tetrazol-5-yl-CH(CH₃)-NH-S(O)₂-* | H | H | H | Cl | Cl |
| 47 | S(O)₂NH(CH₂)₂NS(O)₂N(CH₃)₂ | H | H | H | Cl | Cl |
| 48 | *-CH₂-C(O)-morpholine | H | H | H | Cl | Cl |
| 49 | CH₂C(O)NHCH₂CH₂OH | H | H | H | Cl | Cl |
| 50 | CH=CHCOOH | H | H | H | Cl | Cl |
| 51 | S(O)₂CH₂COOH | H | H | H | Cl | Cl |
| 52 | CH₂C(O)N(CH₃)—(CH₂)₂OH | H | H | H | Cl | Cl |
| 53 | *-CH₂-C(O)-N(CH₃)-CH₂-(furan-3-yl) | H | H | H | Cl | Cl |
| 54 | *-CH₂-C(O)-piperidine-3-C(O)NH₂ | H | H | H | Cl | Cl |
| 55 | CH₂C(O)N(CH₂CH₂OCH₃)₂ | H | H | H | Cl | Cl |
| 56 | CH₂C(O)NHCH₂CH₂OCH₃ | H | H | H | Cl | Cl |
| 57 | *-CH₂-C(O)-NH-CH₂-(tetrahydrofuran-2-yl) | H | H | H | Cl | Cl |
| 58 | *-CH₂-C(O)-NH-CH₂-(4-sulfamoylphenyl) | H | H | H | Cl | Cl |

TABLE 1-continued
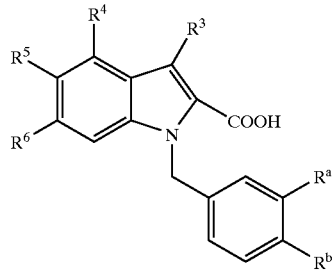
| Compd No. | R³ | R⁴ | R⁵ | R⁶ | Rᵃ | Rᵇ |
|---|---|---|---|---|---|---|
| 59 | 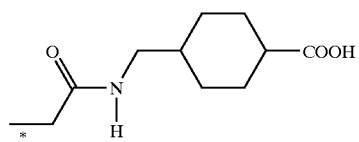 | H | H | H | Cl | Cl |
| 60 | 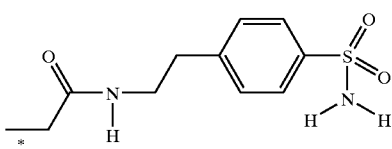 | H | H | H | Cl | Cl |
| 61 | 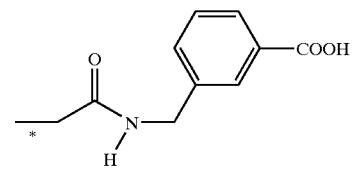 | H | H | H | Cl | Cl |
| 62 | $CH_2C(O)NHCH_2C(O)(CH_2)_2COOH$ | H | H | H | Cl | Cl |
| 63 | 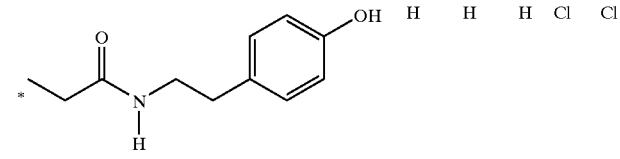 | H | H | H | Cl | Cl |
| 64 | 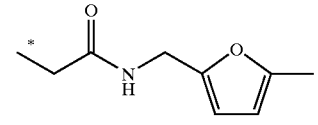 | H | H | H | Cl | Cl |
| 65 | 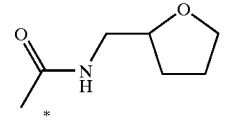 | H | H | H | Cl | Cl |
| 66 | $O(CH_2)_2OCH_3$ | H | H | H | Cl | Cl |
| 67 | $OCH_2CH_2NHC(O)OC(CH_3)_3$ | H | H | H | Cl | Cl |
| 68 |  | H | H | H | Cl | Cl |
| 69 | $OCH_2CH_2NH_2$ | H | H | H | Cl | Cl |

TABLE 1-continued

| Compd No. | R³ | R⁴ | R⁵ | R⁶ | Rᵃ | Rᵇ |
|---|---|---|---|---|---|---|
| 70 | (2,2-dimethyl-1,3-dioxolan-4-yl)methoxy | H | H | H | Cl | Cl |
| 71 | OCH₂CHOHCH₂OH | H | H | H | Cl | Cl |
| 72 | 4-methylmorpholine | H | H | H | Cl | Cl |
| 73 | N-methyl-N-(benzoxazol-2-yl)aminoethoxy | H | H | H | Cl | Cl |
| 74 | 2-dimethylamino-6-methyl-3-(2-methoxyethyl)pyrimidin-4(3H)-one | H | H | H | Cl | Cl |
| 75 | (3-isopropyl-2-oxo-oxazolidin-5-yl)methoxy | H | H | H | Cl | Cl |
| 76 | N-phenyl-N-(2-methoxyethyl)acetamide | H | H | H | Cl | Cl |
| 77 | (furan-3-yl)methoxy | H | H | H | Cl | Cl |
| 78 | (cyclohex-2-enyl)methoxy | H | H | H | Cl | Cl |
| 79 | (4-hydroxymethylcyclohexyl)methoxy | H | H | H | Cl | Cl |

TABLE 1-continued

| Compd No. | R³ | R⁴ | R⁵ | R⁶ | Rᵃ | Rᵇ |
|---|---|---|---|---|---|---|
| 80 | *-O-CH₂CH₂-(4-Cl-phenyl) | H | H | H | Cl | Cl |
| 81 | 3-(acetamido)-tetrahydrothiophene-1,1-dioxide (via NH) | H | H | H | Cl | Cl |
| 82 | OCH₂CH₂OCH₂CH₃ | H | OCH₃ | H | Cl | Cl |
| 83 | OCH₂CH₂OH | H | OCH₃ | H | Cl | Cl |
| 84 | 4-(1,1-dioxo-thiomorpholinyl)carbonylmethyl | H | H | H | Cl | Cl |
| 85 | *-CH₂-NH-C(O)-CH₂-(3,5-dimethylisoxazol-4-yl) | H | H | H | Cl | Cl |
| 86 | COOH | H | H | H | Cl | Cl | where * indicates the point of attachment of the group to the indole ring.

Some compounds of formula (I) have not been proposed hitherto for use as pharmaceuticals. Thus a further aspect of the invention provides a compound for use in therapy, said compound comprising a compound of formula (IA) which is a compound of formula (I) as defined above subject to the following provisos:

(i) when R² is carboxy or a salt or amide thereof, at least three of R⁴, R⁵, R⁶ and R⁷ are hydrogen, and R³ is S(O)qR¹⁵, R¹⁵ is other than $C_{1-4}$ alkyl substituted by carboxy or an ester or amide derivative thereof;

(ii) when R³ is a group NHCOR¹⁶ or NHSO₂R¹⁶, R¹⁶ is optionally substituted alkyl; and (iii) where R³ is a group SR¹⁴ where R¹⁴ is 2-quinolylmethyl, R² is COOH or an ethyl ester thereof, each of R⁴, R⁵, and R⁷ are hydrogen, R¹ is 4-chlorophenyl, R⁶ is other than 2-quinolylmethyl.

Yet a further aspect of the invention provides pharmaceutical compositions comprising a compound of formula (IA) as defined above.

Certain compounds of formula (I) are novel and these form a further aspect of the invention. Thus the invention further provides a compound of formula (IB) which is a compound of formula (IA) as defined above, subject to the following further provisos:

(iv) where R³ is a group CH₂COOH, R² is COOH and each of R⁴, R⁵, R⁶ and R⁷ are hydrogen, R¹ is other than unsubsituted phenyl; and (v) where R³ is a group CH₂COOH, R² is COOH and each of R⁴, R⁵, and R⁷ are hydrogen, R¹ is 4-chlorophenyl, R⁶ is other than methoxy; and (vi) when R³ is OR¹⁵ or S(O)qR¹⁵, R¹⁵ is other than $C_{1-6}$ haloalkyl.

Yet a further proviso which is suitably applied to formula (IB) is (vii) when R² is COOCH₂CH₃, each of R⁴, R⁵, R⁶ and R⁷ are hydrogen and R¹ is 4-chlorophenyl, R³ is other than a group CH=CH(CN)₂.

Furthermore, the proviso (iv') suitably applies to (IA) in that where $R^3$ is a group COOH, $R^2$ is COOH and each of $R^4$, $R^5$, $R^6$ and $R^7$ are hydrogen, $R^1$ is other than unsubsituted phenyl.

Particularly preferred substituents and groups on the compounds of formula (IA) and (IB) are those described above in relation to formula (I).

Suitable examples of compounds of formula (IB) are compounds where $R^3$ is a group $OR^{15}$ straight or branched chain alkyl group which carries at least one hydroxy group, for example from 1 to 4 hydroxy groups, for example 1 or 2 hydroxy groups. Other substituents, as defined above, may be provided on the alkyl chain.

Preferably $R^3$ is a group of formula —O(CH$_2$)$_a$[(CHOH)(CH$_2$)$_b$]$_d$CH$_2$OH where a is 0 or an integer of from 1 to 4, b is 0 or an integer of from 1 to 3, and d is 0 or 1.

Examples of such $R^3$ include OCH$_2$CHOHCH$_2$OH and OCH$_2$CH$_2$OH.

Compounds of formula (I) are suitably prepared by methods such as those described in International Patent Application Nos. PCT/GB98/02340 and PCT/GB98/02341.

In particular compounds of formula (I) can be prepared by reacting a compound of formula (VII)

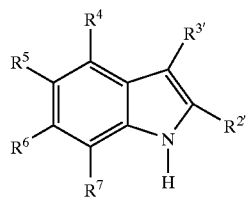

(VII)

where $R^4$, $R^5$, $R^6$ and $R^7$ are as defined in relation to formula (I), $R^{2'}$ is a group $R^2$ as defined in relation to formula (I) or a protected form thereof, and $R^{3'}$ is a group $R^3$ as defined in relation to formula (I) or a precursor thereof; with compound of formula (VIII)

(VIII)

where $R^1$ and X are as defined in relation to formula (I) and $Z^1$ is a leaving group; and thereafter if desired or necessary carrying out one or more of the following steps:

(i) changing a precursor group $R^{3'}$ to a group $R^3$ or a group $R^3$ to a different such group;

(ii) removing any protecting group from $R^{2'}$.

Suitable leaving groups for Z include halide such as chloride, bromide or iodide, as well as mesylate or tosylate. The reaction is suitably effected in an organic solvent such as dimethylformamide (DMF) tetrahydrofuran (THF) or DCM in the presence of a base such as sodium hydride, sodium hydroxide, potassium carbonate. Optionally the reaction is effected in the presence of a suitable phase transfer catalyst. The choice of base and solvent is interdependent to a certain extent in that certain solvents are compatible with some bases only as is understood in the art. For example, sodium hydride may preferably be used with dimethylformamide or tetrahydrofuran and sodium hydroxide is preferably used with dichloromethane and a phase transfer catalyst.

The reaction can be carried out at moderate temperatures, for example from 0 to 50° C. and conveniently at about ambient temperature.

Preferably, $R^{2'}$ is an ester group in the compound of formula (VII) and this may be subsequently converted to an acid or to another ester or salt, by conventional methods. For example, when X is a group SO$_2$ and $R^2$ is a methyl ester of carboxy, it may be converted to the corresponding carboxylic acid by reaction with lithium iodide in dry pyridine or DMF.

Optional step (i) and (ii) above can be carried out using conventional methods. These will depend upon the precise nature of the groups $R^3$, $R^{3'}$, $R^2$ and $R^{2'}$ in each case. Examples of suitable reactions are illustrated hereinafter.

Alternatively, compounds of formula (I) may be prepared by reacting a compound of formula (IX)

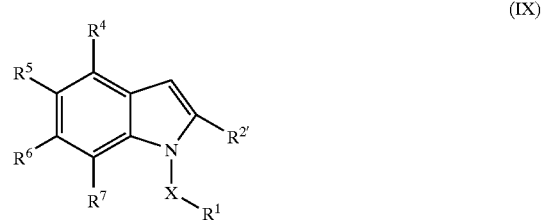

(IX)

where X, $R^1$, R4, $R^5$, $R^6$ and $R^7$ are as defined in relation to formula (I), $R^{2'}$ is a group $R^2$ as defined in relation to formula (I) or a protected form thereof: with a compound of formula (X)

(X)

where $R^{3'}$ is a group $R^3$ as defined in relation to formula (I) or a precursor thereof; and thereafter if desired or necessary carrying out steps (i) and/or (ii) above.

The reaction is suitably carried out in an organic solvent which will depend upon the nature of the compound of formula (IX). Suitable leaving groups $Z^1$ include those listed above for Z.

Compounds of formula (IX) may suitably be prepared by methods analogous to those described above between the compound of formula (VII) and (VIII), although in this case, a compound of formula (VIIA) will be used.

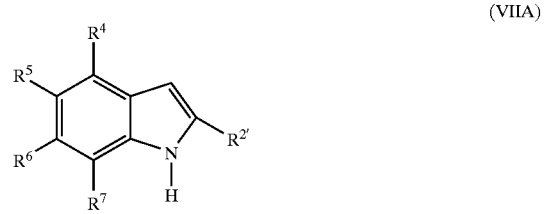

(VIIA)

In this compound, $R^{2'}$, $R^4$, $R^5$, $R^6$ and $R^7$ are as defined above.

Compounds of formula (VII) and (VIIA) may be prepared by cyclisation of a compound of formula (XI)

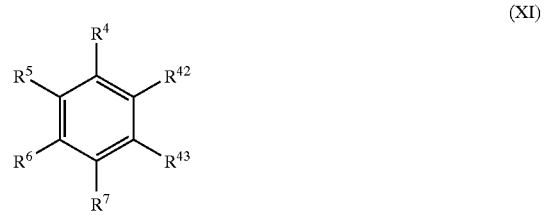

(XI)

where $R^4$, $R^5$, $R^6$ and $R^7$ are as defined above and $R^{42}$ and $R^{43}$ represent a combination of moieties which can cyclise to form an appropriately substituted pyrrole ring. For example, $R^{42}$ can be a group of formula —CH=C($R^{44}$)N$_3$ where $R^{44}$ is a group $R^2$ as defined above, or a protected form thereof, and $R^{43}$ may be hydrogen. Cyclisation to form a compound of formula (XII) may then be effected by heating for example under reflux in an organic solvent, in particular a high boiling aprotic solvent such as xylene or toluene.

Alternatively, $R^{43}$ may be nitro and $R^{42}$ may be a group of formula —$CH_2C(O)R^{2'}$ where $R^{2'}$ is as defined above in relation to formula (VII). These compounds will cyclise in the presence of a catalyst such as palladium on carbon in the presence of hydrogen. The reaction may be effected at moderate temperatures for example of from 0 to 80° C., conveniently at about ambient temperature.

Thus examples of compounds of formula (XI) include compounds of formula (XII) and (XIII)

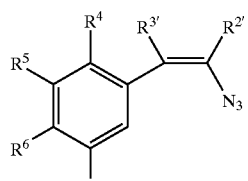
(XIII)

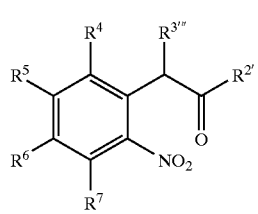
(XIV)

where $R^{2'}$, $R^4$, $R^5$, $R^6$ and $R^7$ are as hereinbefore defined and $R^{3''}$ is a group $R^{3'}$ or is hydrogen, which may be converted later to a group $R^3$ or $R^{3'}$.

Compounds of formula (XIII) where $R^{3'}$ is hydrogen may be prepared for example by reacting a compound of formula (XV)

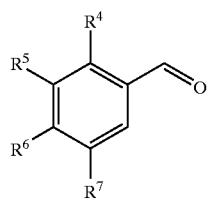
(XV)

with a compound of formula (XVI)

 (XVI)

where $R^4$, $R^5$, $R^6$, $R^7$, and $R^{2'}$ are as defined hereinbefore. The reaction may be effected in an organic solvent such as ethanol at low temperatures of from −20 to 0° C., suitably at about 0° C. The reaction is suitably effected in the presence of a base such as an alkoxide, in particular an ethoxide, for example potassium ethoxide.

Compounds of formula (XVI) are suitably prepared by reacting a compound of formula (XVII)

 (XVII)

where $R^3$ and $R^{2'}$ are as defined above and $R^{47}$ is a leaving group such as halide and in particular bromide, with an azide salt, such as an alkali metal azide salt in particular sodium azide.

Compounds of formula (XIV) may be prepared by reacting a compound of formula (XVIII)

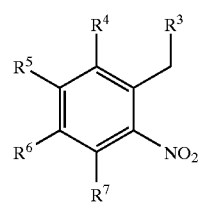
(XVIII)

where $R^5$, $R^6$, $R^7$, $R^3$, $R^4$ and $R^{2'}$ are as defined above, with a compound of formula (XIX)

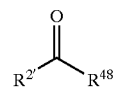
(XIX)

where $R^{2'}$ is as defined above and $R^{48}$ leaving group such as hydroxy. Examples of compounds of formula (XVI) are oxalates such as diethyloxalate. The reaction is suitably effected in the presence of a base such as sodium hydride in an organic solvent such as THF. Moderate temperatures of from 0° to 40° C. and conveniently ambient temperature is employed.

According to a further aspect of the invention there is provided a compound of the formula (I) as defined herein, or a pharmaceutically acceptable salt or an in vivo hydrolysable ester thereof, for use in a method of treatment of the human or animal body by therapy. In particular, the compounds are used in methods of treatment of inflammatory disease.

According to a further aspect of the present invention there is provided a method for antagonising an MCP-1 mediated effect in a warm blooded animal, such as man, in need of such treatment, which comprises administering to said animal an effective amount of a compound of formula (I), or a pharmaceutically acceptable salt, or an in vivo hydrolysable ester thereof.

The invention also provides a compound of formula (I) as defined herein, or a pharmaceutically acceptable salt, or an in vivo hydrolysable ester thereof, for use as a medicament.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch;

lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30$\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The invention is further illustrated, but not limited by the following Examples in which the following general procedures were used unless stated otherwise.

Preparation 1

Ethyl 3-bromoindole-2-carboxylate

A solution of bromine (2.72 ml) in DMF was added dropwise over 10 mins to a solution of ethyl indole-2-carboxylate in DMF. The reaction was stirred for 30 mins, then poured into water to precipitate a pale yellow solid which was filtered off and recrystallized from ethyl acetate to give the desired starting material as white needles (10.2 g, 72%), mp 150–151°; NMR d (CDCl$_3$) 1.44 (t, 3H), 4.45 (q, 2H), 7.22 (m, 1H), 7.38 (m, 2H), 7.66 (d, 1H), 9.27 (brs, 1H); M/z (−) 268 (M$^+$), 266, 196, 194.

Preparation 2

Ethyl 3-benzylthioindole-2-carboxylate

Potassium carbonate (3.5 g) was added to a solution of ethyl 3-bromoindole-2-carboxylate (5.4 g) and benzyl mercaptan (3.05 ml) in DMF (100 ml), and the reaction heated at 100° C. for 3 hours. The reaction was then cooled, poured into water and extracted with ethyl acetate. Combined organic extracts were washed with water and brine, dried (MgSO$_4$) and concentrated in vacuo. The residue was purified by column chromatography using iso-hexane:5% ethyl acetate as eluent, to give the product as a white crystalline solid (3.48 g, 56%); NMR d (CDCl$_3$) 1.42 (t, 3H), 4.05 (s, 2H), 4.40 (q, 2H), 7.10–7.40 (m, 8H), 7.78 (d, 1H), 9.06 (brs, 1H); M/z (+) 312 (MH$^+$), 266, 166.

Preparation 3

Ethyl 3-(ethoxycarbonylmethylthio)indole-2-carboxylate

To a solution of ethyl 3-bromoindole-2-carboxylate (1.34 g) and ethyl 2-mercaptoacetate (0.96 ml) in acetone (15 ml) was added potassium carbonate (1.38 g) and the resulting mixture was heated at reflux under argon for 18 hours. The cooled mixture was poured into water and extracted with ethyl acetate. Combined organic extracts were dried (MgSO$_4$) and concentrated to a gum which was purified by column chromatography using iso-hexane:ethyl acetate (1:4) to give the desired product (331 mg, 21%) NMR d (CDCl$_3$) 1.05 (t, 3H), 1.45 (t, 3H), 3.6 (s, 2H), 4.0 (q, 2H), 4.5 (q, 2H), 7.2–7.4 (m, 3H), 7.9 (d, 1H), 9.2 (brs, 1H); M/z (+) 308.3 (MH$^{30}$).

Preparation 4

Ethyl N-(3,4-dichlorobenzyl)-3-(morpholinosulphinyl) indole-2-carboxylate

Thionyl chloride (5 ml) was added in one portion to a solution of ethyl N-(3,4-dichlorobenzyl)indole-2-carboxylate (908 mg) and the resulting mixture was stirred for 18 hours. The mixture was concentrated in vacuo. The resulting gum was suspended in diethyl ether (12 ml) and morpholine (2.2 ml) was added in one portion. The mixture was stirred for 3 hours. The reaction was quenched with water (10 ml) extracted with dichloromethane, dried (MgSO$_4$) and concentrated to a gum which was purified by column chromatography using iso-hexane:ethyl acetate (1:1) as eluent to give the desired product (907 mg, 72%); NMR d (CDCl$_3$) 1.4 (t, 3H), 3.0–3.1 (m, 2H), 3.3–3.4 (m, 2H), 3.7–3.8 (m, 4H), 4.4 (q, 2H), 5.7 (q, 2H), 6.8 (d, 1H), 7.1 (d, 1H), 7.25–7.4 (m, 4H), 8.6 (d, 1H); M/z (−) 480 (M$^+$).

Preparation 5

The procedure described in Preparation 4 above was repeated using the appropriate amine. Thus was obtained the compound described below.

Ethyl N-(3,4-dichlorobenzyl)-3-(1,1-dioxidothiomorpholino)sulphinylindole-2-carboxylate 52% yield; NMR d (CDCl$_3$) 1.4 (t, 3H), 3.1–3.3 (m, 4H), 3.7–4.0 (4H, m), 4.4 (q, 2H), 5.7 (q, 2H), 6.8 (d, 1H), 7.1 (s, 1H), 7.3–7.5 (m, 4H), 8.6 (d, 1H); M/z (−) 529.1 (M$^+$), 527.1.

Preparation 6

N-(3,4-Dichlorobenzyl)-2-ethoxycarbonylindole-3-sulphinic acid

Ethyl N-(3,4-dichlorobenzyl)indole-2-carboxylate (1.11 g) in thionyl chloride (4.0 ml) was stirred for 16 hours, then concentrated in vacuo. The residue was dissolved in THF (10 ml) and water (2 ml), and stirred for a further 2 hours. The reaction was partitioned between ether and water. Combined organic extracts were dried (MgSO$_4$) and concentrated in vacuo and the residue triturated with ether to give the product as a white solid (0.67 g, 51%); NMR d (CD$_3$SOCD$_3$) 1.27 (t, 3H), 4.35 (q, 2H), 5.80 (s, 2H), 6.83 (d, 1H), 7.23 (t, 1H), 7.40 (m, 2H), 7.57 (d, 1H), 7.68 (d, 1H), 8.42 (d, 1H); M/z (−) 412 (M$^+$), 410, 348, 346.

Preparation 7

N-(3,4-Dichlorobenzyl)-2-ethoxycarbonylindole-3-sulphonyl chloride

N-(3,4-Dichlorobenzyl)-2-ethoxycarbonylindole-3-sulphinic acid (0.48 g), N-chlorosuccinimide (0.16 g) and triethylamine (0.16 ml) were stirred in dichloromethane for 4 hours. The reaction was then concentrated in vacuo and the residue purified by chromatography using iso-hexane:10% ethyl acetate as eluent to give the product as a white crystalline solid (0.27 g, 52%); NMR d (CD$_3$SOCD$_3$) 1.43 (t, 3H), 4.48 (q, 2H), 5.53 (s, 2H), 6.98 (m, 1H), 7.30–7.50 (m, 5H), 8.22 (m, 1H); M/z (−) 444 (M–H$^+$), 426, 410.

Preparation 8

Ethyl 3-diazoindole-2-carboxylate

Acetic acid (77 ml) was added dropwise to a suspension of sodium nitrite (82 g) and ethyl indole-2-carboxylate (25 g) in dichloromethane (1000 ml), and stirred at ambient temperature under inert atmosphere. After 2 days, further sodium nitrite (20 g) was added, and acetic acid (19 ml) was added dropwise, and the reaction left stirring for a further day. The reaction was poured into water (300 ml), extracted with dichloromethane (2×200 ml), and neutralised with saturated sodium hydrogen carbonate solution (300 ml). Combined organic extracts were dried (MgSO$_4$), and concentrated in vacuo to afford the product as a yellow solid (26.96 g, 95%), NMR d (CD$_3$SOCD$_3$) 1.34 (t, 3H), 4.37 (q, 2H), 7.38 (m, 2H), 7.84 (m, 2H); M/z (+) 216.2 (MH$^{30}$).

Preparation 9

Ethyl 3-diazo-5-methoxyindole-2-carboxylate (precursor to compound 83, 84)

To a solution of ethyl 5-methoxyindole-2-carboxylate (8.0 g) in acetone (300 ml) was added a solution of sodium nitrite (39 g) in water (100 ml) and the reaction stirred vigorously while adding dropwise HCl (2M, 98 ml) at 20–25° C. during one hour. The mixture was stirred in a stoppered flask at 20°

C. overnight and the resulting yellow precipitate was filtered to give the product (6.0 g, 67%); NMR d (CDCl$_3$) 1.45 (t, 3H), 3.87 (s, 3H), 4.50 (q, 2H), 6.98 (m, 2H), 7.85 (d, 1H); M/z (+) 246 (MH$^+$).

Preparation 10
s-Butyl 3-bromo-N-(3,4-dichlorobenzyl)indole-2-carboxylate

N,N-dimethylformamide di-t-butyl acetal (19.90 ml) was added dropwise to a suspension of 3-bromo-N-(3,4-dichlorobenzyl)indole-2-carboxylic acid (8.31 g) in toluene (150 ml), under an atmosphere of argon, and stirred at ambient temperature for 2 hours. The reaction was cooled, filtered, and washed with brine (100 ml), saturated NaHCO$_3$ (aq.) (100 ml), and brine (100 ml), dried (MgSO$_4$) and concentrated in vacuo to afford the product as a clear oil that crystallised upon standing (7.65 g, 81%); NMR d (CD$_3$SOCD$_3$) 1.49 (s, 9H), 5.76 (s, 2H), 6.86 (m, 1H), 7.24 (t, 1H), 7.35–7.68 (m, 5H); M/z (+) 456 (MH$^-$), 400.

Preparation 11
Methyl 2-methoxycarbonyl-3-indoleacetate

Phenyl hydrazine (5.7 ml), dimethyl 2-oxoglutarate (10 g) and acetic acid (1.0 ml) in methanol (100 ml) were heated at reflux for 1 hour, then concentrated in in vacuo. The crude hydrazone (13 g) was dissolved in saturated methanolic hydrochloric acid (350 ml) and heated to 75° C. for 16 hours with continual stirring. The reaction was diluted with water (200 ml) and extracted with dichloromethane. Combined organic extracts were washed with saturated aqueous sodium hydrogencarbonate solution, water, saturated aqueous sodium chloride solution and dried (MgSO$_4$). The solvent was removed in vacuo to give a yellow crystalline solid (7.0 g); NMR d (CD$_3$SOCD$_3$) 3.59 (s, 3H), 3.83 (s, 3H), 4.12 (s, 2H), 7.06 (t, 1H), 7.26 (t, 1H), 7.41 (d, 1H), 7.63 (d, 1H), 11.76 (brs, 1H); M/z (−) 246 (M−H$^+$).

Preparation 12
Methyl N-(3,4-dichlorobenzyl)-2-methoxycarbonyl-3-indoleacetate 3,4-Dichlorobenzyl chloride (8.2 g) was added to a stirred solution of methyl 2-methoxycarbonyl-3-indoleacetate (6.5 g) and potassium carbonate (8.36 g) in acetonitrile (200 ml) under an atmosphere of argon. The reaction was heated to 80° C. for 24 hours. The reaction was concentrated in vacuo and partitioned between ethyl acetate and water. Combined organic extracts were washed with saturated aqueous sodium chloride solution, dried (MgSO$_4$) and concentrated in vacuo. The residue was purified by column chromatography using 25% ethyl acetate:iso-hexane as eluent to give the product as a white solid (6.95 g, 65%), NMR d (CD$_3$SOCD$_3$) 3.60 (s, 3H), 3.77 (s, 3H), 4.13 (s, 2H), 5.89 (s, 2H), 6.89 (dd, 1H), 7.16 (t, 1H), 7.27 (d, 1H), 7.34 (t, 1H), 7.52 (d, 1H), 7.57 (d, 1H), 7.78 (d, 1H); M/z (+) 406 (MH$^+$).

Preparation 13
Methyl 3-aminoindole-2-carboxylate

To a solution of ethyl 3-aminoindole-2-carboxylate [Prepared according to P. Unangst. *J. Het. Chem.*, 1983, 20, 495] (5.0 g) in methanol (50 ml) was added sodium methoxide (6.5 g). The resulting mixture was stirred for 4 hours and then quenched with saturated ammonium chloride solution. The resulting mixture was extracted with dichloromethane, dried (MgSO$_4$) and evaporated to give a gum which was purified by column chromatography using iso-hexane:ethyl acetate (1:4) as eluent to give the desired product (1.95 g, 42%); NMR d (CD$_3$SOCD$_3$), 3.8 (s, 3H), 5.7 (s, 2H), 6.8–6.9 (m, 1H), 7.2 (m, 2H), 7.7 (d, 1H); M/z (+) 191.1 (MH$^+$).

Preparation 14
Ethyl 3-formylindole-2-carboxylate

A mixture of N-methylformanilide (2.25 ml) and phosphoryl chloride (1.70 ml) was stirred at ambient temperature for 15 minutes. 1,2-dichloroethane (30 ml) was then added, followed by ethyl indole-2-carboxylate (3 g) and the reaction was heated at reflux for 90 minutes. The reaction mixture was then poured into a mixture of ice/water (200 ml) and sodium acetate (10 g) and extracted with ethyl acetate (2×200 ml). Combined organic phases were evaporated and the crude residue purified by column chromatography using dichloromethane as eluent to give the product as a white solid (2.27 g, 66%); NMR d (CD$_3$SOCD$_3$) 1.40 (t, 3H), 4.42 (q, 2H), 7.25 (m, 1H), 7.40 (m, 1H), 7.55 (m, 1H), 8.20 (m, 1H), 12.77 (s, 1H); M/z (+) 218.3 (MH$^+$).

Preparation 15
Ethyl 3-formyl-N-(3,4-dichlorobenzyl)indole-2-carboxylate

Sodium hydride (488 mg, 60% in mineral oil) was added to a stirred solution of ethyl 3-formylindole-2-carboxylate (2.21 g) in DMF (100 ml) under argon, and reaction stirred at ambient temperature for 25 minutes. 3,4-Dichlorobenzyl chloride (1.71 ml) was then added and the reaction stirred overnight. The reaction mixture was concentrated in vacuo and the residue dissolved in ethyl acetate (80 ml) and washed with water (2×80 ml), dried (MgSO$_4$) and concentrated in vacuo to give a crude residue which was purified by column chromatography using ethyl acetate:iso-hexane as eluent (gradient 5/95–100/0), to give the product as a yellow solid (2.17 g, 57%); NMR d (CD$_3$SOCD$_3$) 1.25 (t, 3H), 4.40 (q, 2H), 5.80 (s, 2H), 7.00 (m, 1H), 7.30–7.50 (m, 3H), 7.55 (m, 1H), 7.65 (m, 1H), 8.35 (m, 1H), 10.48 (s, 1H); M/z (+) 376.4 (MH$^+$).

Preparation 16
Ethyl N-(3,4-dichlorobenzyl)-2-ethoxycarbonylindole-3-carboxylate A mixture of sodium chlorite (3.39 g) and sodium dihydrogen orthophosphate (4.54 g) in water (50 ml) was added dropwise to a stirred solution of ethyl 3-formyl-N-(3,4-dichlorobenzyl)indole-2-carboxylate (1.56 g) and 2-methylbut-2-ene (50 ml) in tert-butyl alcohol (100 ml) at ambient temperature and reaction stirred vigorously overnight. The reaction mixture was concentrated in vacuo and the residue dissolved in dichloromethane (100 ml), washed with water (100 ml), dried (MgSO$_4$) and concentrated in vacuo to give the product as a yellow solid (1.50 g, 92%); NMR d (CD$_3$SOCD$_3$) 1.20 (t, 3H), 4.30 (q, 2H), 5.50 (s, 2H), 7.00 (m, 1H), 7.25 (m, 2H), 7.42 (m, 1H), 7.58 (m, 2H), 8.00 (m, 1H), 12.68 (s, 1H); M/z (−) 390.4 (M−H$^+$).

EXAMPLE 1
Ethyl N-(3,4-dichlorobenzyl)-3-benzylthioindole-2-carboxylate (Ethyl ester of Compound 5)

Powdered sodium hydroxide (3.2 g) was added in a single portion to a vigorously stirred solution of ethyl 3-benzylthioindole-2-carboxylate (2.48 g), 3,4-dichlorobenzyl chloride (1.71 g) and tetra-n-butylammonium hydrogensulphate (0.5 g) in dichloromethane (100 ml). The reaction was stirred for 6 hours then partitioned between 2M HCl and ethyl acetate. Combined organic extracts were dried (MgSO$_4$) and concentrated in vacuo and the residue purified by column chromatography using iso-hexane:5% ethyl acetate as eluent to give the product as a white crystalline solid (2.26 g, 60%); NMR d (CD$_3$SOCD$_3$) 1.32 (t, 3H), 4.00 (s, 2H), 4.25 (q, 2H), 5.60 (s, 2H), 6.78 (d, 1H), 7.04 (m, 2H), 7.10–7.38 (m, 8H), 7.80 (d, 1H); M/z (+) 470 (M$^+$), 426, 424.

EXAMPLE 2

The procedure described in Example 1 above was repeated using the appropriate indole. Thus were obtained the compounds described below.

Ethyl 3-bromo-N-(3,4-dichlorobenzyl)indole-2-carboxylate (Precursor to Compound 73)

98% yield; NMR d (CD$_3$SOCD$_3$) 1.26 (t, 3H), 4.30 (q, 2H), 5.79 (s, 2H), 6.89 (d, 1H), 7.25 (s, 1H), 7.33–7.46 (m, 2H), 7.50 (d, 1H), 7.57–7.68 (m, 2H), M/z (+) 430.1 (MH$^+$).

Ethyl N-(3,4-dichlorobenzyl)-3-(2,2-dimethyl-1,3-dioxolane-4-ylmethoxy)indole-2-carboxylate (Ethyl ester of Compound 70)

71% yield; NMR d (CD$_3$SOCD$_3$) 1.26 (t, 3H), 1.29 (s, 3H), 1.34 (s, 3H), 3.84 (t, 1H), 4.10 (m, 1H), 4.25 (q, 2H), 4.42 (m, 1H), 571 (s, 2H), 6.86 (m, 1H), 7.13 (t, 1H), 7.32 (m, 2H), 7.53 (m, 2H), 7.77 (d, 1H); M/z (+) 478.3 (MH$^+$).

Ethyl N-(3,4-dichlorobenzyl)-3-[2-(N-acetyl-N-phenylamino)ethoxy]indole-2-carboxylate (Ethyl ester of Compound 76)

82% yield; NMR d (CD$_3$SOCD$_3$) 1.22 (t, 3H), 3.27 (s, 3H), 3.44 (t, 2H), 4.15 (t, 2H), 4.25 (q, 2H), 5.70 (s, 2H), 6.85 (d, 1H), 7.10 (t, 1H), 7.27 (m, 7H), 7.53 (m, 2H), 7.64 (d, 2H); M/z (+) 525.5 (MH$^+$).

Ethyl N-(3,4-dichlorobenzyl)-3-(3-furylmethoxy)indole-2-carboxylate (Ethyl ester of Compound 77)

64% yield; NMR d (CD$_3$SOCD$_3$) 1.23 (t, 3H), 4.24 (q, 2H), 5.09 (s, 2H), 5.71 (s, 2H), (s, 1H), 6.83 (d, 1H), 7.10 (t, 1H), 7.29 (m, 2H), 7.51 (t, 2H), 7.65 (m, 3H); M/z (+) 444.4 (MH$^+$).

Ethyl N-(3,4-dichlorobenzyl)-3-(cyclohex-2-enylmethoxy)indole-2-carboxylate (Ethyl ester of Compound 78)

83% yield; NMR d (CD$_3$SOCD$_3$) 1.24 (t, 3H), 1.42 (m, 1H), 1.91 (m, 2H), 2.04 (m, 3H), 2.19 (m, 1H), 4.10 (m, 2H), 4.25 (q, 2H), 5.68 (s, 2H), 5.70 (s, 2H), 6.84 (d, 1H), 7.13 (t, 1H), 7.32 (m, 2H), 7.52 (m, 2H), 7.74 (d, 1H); M/z (+) 458.4 (MH$^+$).

Ethyl N-(3,4-dichlorobenzyl)-3-[4-(hydroxymethyl)cyclohexylmethoxy]indole-2-carboxylate (Ethyl ester of Compound 79)

69% yield; NMR d (CDCl$_3$) 0.82–2.15 (m, 10H), 1.36 (t, 3H), 3.50 (d, 2H), 4.07 (d, 2H), 4.35 (q, 2H), 5.64 (s, 2H), 6.81 (d, 2H), 7.12 (m, 2H), 7.27 (m, 3H), 7.75 (d, 2H); M/z (+) 490.5 (MH$^+$).

Ethyl N-(3,4-dichlorobenzyl)-3-(4-chlorophenethyloxy)indole-2-carboxylate (Ethyl ester of Compound 80)

87% yield; NMR d (CD$_3$SOCD$_3$) 1.21 (t, 3H), 3.07 (t, 2H), 4.21 (q, 2H), 4.37 (t, 2H), 5.70 (s, 2H), 6.84 (d, 1H), 7.07 (t, 1H), 7.31 (m, 6H), 7.51 (t, 3H); M/z (+) 504.5 (MH$^+$).

Compound 23 ethyl ester

29% yield; NMR d (CDCl$_3$) 1.35 (t, 3H), 3.4 (t, 1H), 3.9–4.0 (m, 2H), 4.3–4.5 (m, 4H), 5.6 (s, 2H), 6.8 (d, 1H), 7.1–7.4 (m, 5H), 7.8 (d, 1H); M/z (+) 410.3 (MH$^+$), 408.2.

Compound 26 ethyl ester

45% yield, NMR d (CDCl$_3$) 1.35 (t, 3H), 3.2 (t, 2H), 4.3 (q, 2H), 4.45 (t, 2H), 5.65 (s, 2H), 6.8 (dd, 1H), 7.05–7.4 (m, 10H), 7.5 (d, 1H); M/z (+) 470.3 (MH$^+$), 468.4.

2-ethyl ester & methyl ester of Compound 27

66% yield; M/z (+) 438.3 (MH$^+$), 436.2.

Ethyl ester of Compound 66

62% yield; NMR d (CDCl$_3$) 1.4 (t, 3H), 3.5 (s, 3H), 4.3–4.4 (m, 4H), 5.65 (s, 2H), 6.85 (dd, 1H), 7.1–7.4 (m, 5H), 7.8 (d, 1H); M/z (+) 424 (MH$^+$), 422.

Ethyl ester of Compound 67

73% yield; NMR d (CDCl$_3$) 1.4 (t, 3H), 1.5 (s, 9H), 3.7 (q, 2H), 4.4 (q, 2H), 5.65 (s, 2H), 6.8 (dd, 1H), 7.1–7.4 (m, 5H), 7.9 (d, 1H); M/z (+) 507.3 (MH$^+$).

Methyl 3-amino-N-(3,4-dichlorobenzyl)indole-2-carboxylate (Precursor to Compound1,2)

64% yield; NMR d (CD$_3$SOCD$_3$) 3.75 (s, 3H), 5.6 (s, 2H), 6.0 (s, 2H), 6.8–7.0 (m, 2H), 7.1–7.5 (m, 4H), 7.85 (d, 1H); M/z (+) 351.2 (MH$^+$), 349.2.

Di-ethyl ester Compound 24

38% yield; NMR d (CDCl$_3$) 1.05 (t, 3H), 1.4 (t, 3H), 3.6 (s, 2H), 3.95 (q, 2H), 4.4 (q, 2H), 5.7 (s, 2H), 6.85 (dd, 1H), 7.2–7.4 (m, 5H), 7.9 (d, 1H); M/z (+) 468.3 (MH$^+$), 466.3.

Ethyl 3-amino-N-(3,4-dichlorobenzyl)indole-2-carboxylate (Precursor to Compound 8, 9, 10, 11, 12, 13, 14, 15 16, 17, 18, 19, 20, 22)

44% yield; NMR d (CD$_3$SOCD$_3$) 1.21 (t, 3H), 4.21 (q, 2H), 5.56 (s, 2H), 6.00 (s, 2H), 6.86 (d, 1H), 6.98 (t, 1H), 7.22 (d, 1H), 7.30 (t, 1H), 7.40 (d, 1H), 7.48 (d, 1H), 7.86 (d, 1H); M/z (+) 363 (MH$^+$).

EXAMPLE 3

Ethyl ester of Compound 73

Sodium hydride (23 mg, 60% dispersion in mineral oil) was added in a single portion to a stirred solution of compound of formula (A) (0.19 g) in DMF (3.0 ml) and the reaction stirred for 30 mins.

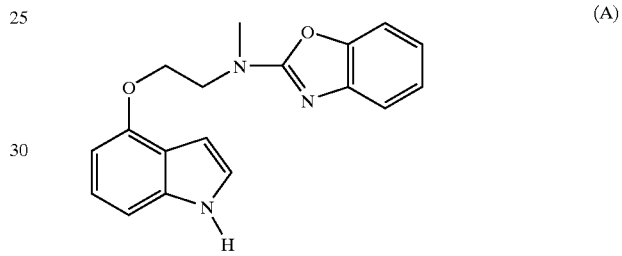

(A)

3,4-Dichlorobenzyl chloride (0.1 ml) was added and the reaction stirred for 16 hours. The reaction was poured into water and extracted with ethyl acetate. Combined organic extracts were dried (MgSO$_4$) and concentrated and the residue purified by chromatography using iso-hexane:20% ethyl acetate as eluent to give the product as a colourless oil (0.23 g, 85%); M/z (+) 540, 538 (MH$^+$).

EXAMPLE 4

The procedure described in Example 3 above was repeated using the appropriate indole. Thus were obtained the compounds described below.

Ethyl ester of Compound 74

93% yield; M/z (+) 545, 543 (MH$^+$).

Ethyl ester of Compound 75

73% yield; M/z (+) 507, 505 (MH$^+$), 461, 459, 318.

Ethyl N-(3,4-dichlorobenzyl)indole-2-carboxylate

60% yield; M/z (+) 349 (MH$^+$)

Diethyl N-(3,4-dichlorobenzyl)-2,3-dicarboxylate

74% yield; M/z (+) 392, 394 (MH$^+$)

EXAMPLE 5

Ethyl N-(3,4-dichlorobenzyl)-3-(2-ethoxyethoxy)-5-methoxyindole-2-carboxylate (Ethyl ester of Compound 82)

To a solution of ethyl N-(3,4-dichlorobenzyl)-3-(2-ethoxyethoxy)-5-methoxyindole-2-carboxylate (3.0 g) in DMF (50 ml) was add anhydrous potassium carbonate (3.0 g), 3,4-dichlorobenzyl chloride (2.0 ml) and potassium iodide (100 mg), and the reaction stirred at 60° C. for 3 hours. The solvent was evaporated in vacuo and the residue partitioned between water (200 ml) and ether (200 ml), the organic layer was dried (MgSO$_4$) and evaporated to give a gum, which was purified by column chromatography using iso-hexane:ethyl acetate (4:1) to give the product (2.5 g, 55%); NMR d (CDCl$_3$) 1.25 (t, 3H), 1.38 (t, 3H), 3.62 (q, 2H), 3.80 (t, 2H), 3.86 (s, 3H), 4.3–4.4 (m, 4H), 5.62 (s, 2H), 6.80 (dd, 1H), 7.12 (s, 1H), 7.14 (d, 1H), 7.20 (d, 1H), 7.26 (d, 1H).

EXAMPLE 6

The procedure described in Example 5 above was repeated using the appropriate indole and benzyl halide. Thus was obtained the compound described below.
Ethyl N-(3,4-dichlorobenzyl)-3-(2-hydroxyethoxy)-5-methoxyindole-2-carboxylate (Ethyl ester of Compound 83)
38% yield; NMR d (CDCl$_3$) 1.32 (t, 3H), 3.42 (t, 1H), 3.87 (s, 3H), 3.92 (m, 2H), 4.3–4.4 (m, 4H), 5.60 (s, 2H), 6.80 (dd, 1H), 7.02 (dd, 1H), 7.1–7.2 (m, 3H), 7.32 (d, 1H); M/z (+) 440 (MH$^+$), 438.

EXAMPLE 7
N-(3,4-Dichlorobenzyl)-3-benzylsulphinylindole-2-carboxylic acid (Compound 25)

A solution of ethyl N-(3,4-dichlorobenzyl)-3-benzylthioindole-2-carboxylate (0.50 g) in dichloromethane (2 ml) was added to a slurry of wet alumina (1 g) and Oxone® (0.615 g) in dichloromethane (10 ml). The mixture was then heated at reflux for two hours, and allowed to cool. The product was washed away from the alumina using methylene chloride (200 ml). The solution was then dried (MgSO$_4$) and evaporated to afford the crude sulphoxide ester (103 mg). The crude ester was dissolved in THF (2 ml) and methanol (1 ml), and sodium hydroxide (2M, 3 ml) was added. The solution was stirred for five hours, then concentrated in vacuo. The residue was dissolved in water (10 ml) and the product precipitated by dropwise addition of aqueous HCl (2M, 10 ml). The resulting solid was collected by filtration and washed with cold water, then dried in vacuo to afford the product as a pale yellow solid (36 mg, 7%. 2 steps), NMR d (CD$_3$SOCD$_3$) 4.37 (d, 2H), 5.83 (d, 2H), 6.96 (dd, 1H), 7.10 (m, 3H), 7.20 (m, 3H), 7.30 (t, 1H), 7.38 (d, 1H), 7.59 (s, 1H), 7.62 (s, 1H), 8.05 (d, 1H); M/z (–) 456 (M–H$^+$), 412, 365, 323, 321, 320.

EXAMPLE 8
Ethyl N-(3,4-dichlorobenzyl)-3-benzylsulphonylindole-2-carboxylate (Ethyl ester of Compound 21)

To a solution of ethyl N-(3,4-dichlorobenzyl)-3-benzylthioindole-2-carboxylate (520 mg) in acetic acid (12 ml) was added hydrogen peroxide solution (30%, 2.5 ml) and the resulting mixture was stirred for 18 hours. The reaction mixture was poured into water (20 ml), made basic with sodium bicarbonate and extracted with dichloromethane. The organic extracts were dried (MgSO$_4$) and concentrated in vacuo. The residue was purified by column chromatography using iso-hexane:20% ethyl acetate as eluent to give the product as a yellow gum (205 mg, 37%); NMR d (CDCl$_3$) 1.4 (t, 3H), 4.45 (q, 2H), 4.6 (s, 2H), 5.5 (s, 2H), 6.9 (dd, 1H), 7.1–7.3 (m, 9H), 7.4 (d, 1H), 7.7 (d, 1H); M/z (+) 504.3 (MH$^+$), 502.4.

EXAMPLE 9

The procedure described in Example 8 above was repeated using the appropriate thioindole. Thus was obtained the compound described below.
Di-ethyl ester of Compound 51
48% yield; M/z (+) 500.2 (MH$^+$), 498.3.

EXAMPLE 10
N-(3,4-Dichlorobenzyl)-3-benzylthioindole-2-carboxylic acid (Compound 5)

Ethyl N-(3,4-dichlorobenzyl)-3-benzylthioindole-2-carboxylate (0.31 g) was dissolved in THF/methanol (1:1) and sodium hydroxide (2M, 2.0 ml) was added and the reaction stirred for 16 hours. The reaction was then concentrated in vacuo and the residue dissolved in water. The solution was acidified by dropwise addition of acetic acid, resulting in the precipitation of a white solid which was filtered, washed with water and dried in vacuo to give the desired end product (0.082 g, 28%); NMR d (CD$_3$SOCD$_3$) 4.04 (s, 2H), 5.72 (s, 2H), 6.83–7.62 (m, 12H); M/z (–) 442 (M$^+$), 440, 428, 398, 396, 307, 305.

EXAMPLE 11

The procedure described in Example 10 above was repeated using the appropriate ester. Thus were obtained the compounds described below.
Compound 70
70% yield; NMR d (CD$_3$SOCD$_3$) 1.30 (s, 3H), 1.35 (s, 3H), 3.87 (m, 1H), 4.10 (m, 3H), 4.40 (m, 1H), 5.75 (s, 2H), 6.90 (d, 2H), 7.13 (t, 1H), 7.32 (m, 2H), 7.51 (m, 2H), 7.75 (d, 2H); M/z (–) 448.2 (M–H$^+$).
Compound 76
85% yield; NMR d (CD$_3$SOCD$_3$) 3.35 (m, 2H), 3.44 (s, 3H), 5.80 (s, 2H), 7.10 (m, 2H), 7.21 (m, 6H), 7.42 (m, 3H), 7.59 (d, 1H); M/z (–) 495.4 (M–H$^+$).
Compound 77
61% yield; NMR d (CD$_3$SOCD$_3$) 5.10 (s, 2H), 5.77 (s, 2H), 6.58 (s, 1H), 6.89 (d, 1H), 7.07 (t, 1H), 7.27 (m, 2H), 7.50 (m, 2H), 7.62 (m, 3H); M/z (–) 414.2 (M–H$^+$).
Compound 78
57% yield; NMR d (CD$_3$SOCD$_3$) 1.40 (m, 1H), 2.00 (m, 6H), 4.08 (d, 2H), 5.67 (s, 2H), 5.73 (s, 2H), 6.90 (m, 1H), 7.10 (m, 1H), 7.30 (m, 1H), 7.52 (m, 2H), 7.70 (m, 1H); M/z (–) 428.3 (M–H$^+$).
Compound 79
68% yield; NMR d (CD$_3$SOCD$_3$) 0.96 (m, 4H), 1.52 (m, 1H), 1.77 (m, 2H), 1.90 (m, 3H), 3.20 (d, 2H), 3.96 (d, 2H), 5.78 (s, 2H), 7.00 (m, 2 H), 7.15 (t, 1H), 7.35 (m, 2H), 7.50 (m, 2H); M/z (–) 460.4 (M–H$^+$).
Compound 80
65% yield; NMR d (CD$_3$SOCD$_3$) 2.99 (t, 2H), 4.35 (t, 2H), 5.80 (s, 2H), 6.87 (t, 1H), 7.04 (m, 2H), 7.23 (m, 2H), 7.36 (m, 5H), 7.48 (d, 1H); M/z (–) 474.3 (M–H$^+$).
Compound 71
91% yield; NMR d (CD$_3$SOCD$_3$) 3.52 (m, 2H), 3.86 (m, 1H), 4.12 (m, 1H), 4.27 (m, 1H), 5.74 (s, 2H), 6.90 (d, 1H), 7.18 (t, 1H), 7.38 (m, 2H), 7.58 (m, 2H), 7.87 (d, 1H), M/z (–) 408.2 (M–H$^+$).
3-Bromo-N-(3,4-dichlorobenzyl)indole-2-carboxylic acid (Precursor to Compound 72)
90% yield; NMR d (CD$_3$SOCD$_3$) 5.83 (s, 2H), 6.89 (m, 1H), 7.25 (t, 1H), 7.39 (m, 2H), 7.51 (d, 1H), 7.60 (m, 2H); M/z (–) 398.2 (M–H$^+$), 354.3.
Compound 73
48% yield; M/z (–) 510 (M$^+$), 508, 466, 464.
Compound 74
21% yield; M/z (–) 515 (M$^+$), 513, 425, 143.
Compound 75
53% yield; M/z (–) 477 (M$^+$), 475, 431, 290.
N-(3,4-Dichlorobenzyl)-2-carboxylic acid-3-indoleacetic acid (Compound 28)
92% yield; NMR d (CD$_3$SOCD$_3$) 3.72 (s, 2H), 5.80 (s, 2H), 7.00–7.10 (m, 2H), 7.16 (t, 1H), 7.33–7.40 (m, 2H), 7.49 (d, 1H), 7.58 (d, 1H); M/z (–) 376 (M–H$^+$).

Compound 68
57% yield; NMR d (CD$_3$SOCD$_3$) 1.50–2.00 (m, 4H), 3.60 (q, 1H), 3.80 (q, 1H), 3.90 (m, 1H), 5.75 (s, 2H), 7.10 (m, 3H), 7.35 (d, 1H), 7.45 (s, 1H), 7.50 (d, 1H), 8.25 (d, 1H); M/z (−) 445.2 (M–H$^+$).

Compound 81
93% yield; NMR d (CD$_3$SOCD$_3$) 2.25 (m, 1H), 3.05–3.60 (m, 5H), 4.80 (m, 1H), 5.90 (s, 2H), 7.05 (m, 1H), 7.30 (t, 1H), 7.40 (m, 2H), 7.65 (m, 2H), 7.80 (m, 1H), 8.95 (m, 1H); M/z (−) 479.4 (M–H$^+$).

Compound 84
58% yield; M/z(−) 479.2 (M–H$^+$).

Compound 85
81% yield; M/z (−) 470.2 (M–H$^+$).

(Z)-N-(3,4-Dichlorobenzyl)-2-carboxyindole-3-acrylic acid (Compound 50)
81% yield; NMR d (CD$_3$SOCD$_3$) 5.80 (s, 2H), 6.50 (d, 1H), 6.90 (m, 1H), 7.30 (m, 3H), 7.50 (d, 1H), 7.60 (m, 1H), 8.00 (m, 1H), 8.40 (d, 1H); M/z (−) 388.4 (M–H$^+$).

N-(3,4-Dichlorobenzyl)-3-(2-ethoxyethoxy)-5-methoxyindole-2-carboxylic acid (Compound 82)
60% yield; NMR d (CD$_3$SOCD$_3$) 1.14 (t, 3H), 3.46 (q, 2H), 3.60 (t, 2H), 3.73 (s, 3H), 4.25 (t, 2H), 5.80 (s, 2H), 6.70 (dd, 1H), 6.95 (d, 1H), 7.1–7.2 (m, 2H), 7.32 (d, 1H), 7.46 (d, 1H); M/z (−) 438 (M–H$^+$), 438.

Compound 23
84% yield; NMR d (CD$_3$SOCD$_3$) 3.7 (t, 2H), 4.2 (t, 2H), 5.7 (s, 2H), 6.9 (dd, 1H), 7.1 (t, 1H), 7.3–7.4 (m, 2H), 7.5–7.6 (m, 2H), 7.8 (d, 1H); M/z (−) 380.2 (M$^+$), 378.2.

Compound 26
87% yield; NMR d (CD$_3$SOCD$_3$) 3.1 (t, 2H), 4.35 (t, 2H), 5.7 (s, 2H), 6.9 (dd, 1H), 7.05 (t, 1H), 7.2–7.4 (m, 7H), 7.45–7.76 (m, 4H); M/z (−) 440.2. (M$^+$), 438.1.

Compound 27
94% yield; NMR d (CD$_3$SOCD$_3$) 4.6 (s, 2H), 5.7 (s, 2H), 6.95 (dd, 1H), 7.1 (t, 1H), 7.2 (t, 1H), 7.37 (d, 1H), 7.4–7.5 (m, 2H), 7.7 (d, 1H); M/z (−) 394 (M$^+$), 392.

Compound 66
49% yield; NMR d (CD$_3$SOCD$_3$) 3.6 (t, 2H), 4.25 (t, 2H), 5.85 (s, 2H), 6.9 (t, 1H), 7.0 (t, 1H), 7.1 (dd, 1H), 7.25 (d, 1H), 7.4 (s, 1H), 7.5 (d, 2H); M/z (−) 394.2 (M$^+$), 392.1.

Compound 67
59% yield; NMR d (CD$_3$SOCD$_3$) 1.4 (s, 9H), 3.3 (s, 3H), 4.1 (t, 2H), 5.7 (s, 2H), 6.8–7.0 (m, 2H), 7.1 (d, 1H), 7.3–7.4 (m, 2H), 7.5 (t, 2H), 7.7 (d, 1H); M/z (−) 479.3 (M$^{30}$).

Compound 1
84% yield; NMR d (CD$_3$SOCD$_3$) 5.9 (s, 2H), 6.95 (dd, 1H), 7.1 (t, 1H), 7.3–7.4 (m, 2H), 7.5–7.7 (m, 4H), 7.8 (d, 1H), 8.0 (d, 1H), 8.1 (s, 1H); M/z (−) 473.1 (M$^+$), 471.1.

Compound 2
47% yield; NMR d (CD$_3$SOCD$_3$) 5.85 (s, 2H), 6.95 (d, 1H), 7.1 (t, 1H), 7.3–7.4 (m, 2H), 7.5 (d, 1H), 7.8 (d, 1H); M/z (−) 413.1 (M$^+$), 411.1.

N-(3,4-Dichlorobenzyl)-3-benzylsulphonylindole-2-carboxylic acid (Compound 21)
81% yield; NMR d (CD$_3$SOCD$_3$) 4.8 (s, 2H), 5.7 (s, 2H), 7.0–7.25 (m, 8H), 7.4–7.6 (m, 4H); M/z (+) 474.3 (MH$^+$).

Compound 24
98% yield; NMR d (CD$_3$SOCD$_3$) 3.6 (s, 2H), 5.75 (s, 2H), 6.9 (dd, 1H), 7.2–7.4 (m, 3H), 7.5 (dd, 2H), 7.8 (d, 1H); M/z (−) 410.1 (M$^+$), 408.1.

N-(3,4-Dichlorobenzyl)-3-(2-hydroxyethoxy)-5-methoxyindole-2-carboxylic acid (Compound 83)
93% yield; NMR d (CD$_3$SOCD$_3$) 3.46 (t, 2H), 3.74 (s, 3H), 4.14 (t, 2H), 5.80 (s, 2H), 6.63 (dd, 1H), 7.96 (d, 1H), 7.06 (dd, 1H), 7.20 (d, 1H), 7.30 (s, 1H), 7.46 (d, 1H); M/z (−) 410 (M–H$^+$), 408.

N-(3,4-Dichlorobenzyl)-3-morpholinosulphonylindole-2-carboxylic acid (Compound 3)
59% yield; NMR d (CDCl$_3$) 3.05–3.15 (m, 4H), 3.7–3.8 (m, 4H), 5.7 (s, 2H), 6.9 (dd, 1H), 7.2–7.5 (m, 5H), 8.2 (d, 1H); M/z (+) 471 (MH$^+$), 469.

N-(3,4-Dichlorobenzyl)-3-(1,1-dioxidothiomorpholino)sulphonylindole-2-carboxylic acid (Compound 4)
93% yield; NMR d (CD$_3$SOCD$_3$), 3.1–3.2 (m, 4H), 3.7–3.8 (m, 4H), 5.45 (s, 2H), 7.1–7.2 (m, 2H), 7.3–7.45 (m, 2H), 7.5 (d, 1H), 7.7–7.8 (m, 2H); M/z (+) 519.2 (MH$^+$), 517.2.

Compound 51
23% yield; NMR d (CD$_3$SOCD$_3$), 4.1 (s, 2H), 5.6 (s, 2H), 7.1 (m, 2H), 7.3–7.4 (m, 2H), 7.5 (d, 1H), 7.7 (s, 1H), 7.9 (m, 1H); M/z (−) 442 (M$^+$), 440.

Compound 86
27% yield; NMR d (CD$_3$SOCD$_3$) 6.65 (s, 2H), 7.45 (dd, 1H), 7.6–7.75 (m, 2H), 7.8 (d, 1H), 7.95 (t, 1H), 8.95 (d, 1H); M/z (−) 362, 364 (M$^+$)

EXAMPLE 12

Ethyl N-(3,4-dichlorobenzyl)-3-morpholinosulphonylindole-2-carboxylate [Ethyl ester of Compound 3]

To a suspension of ethyl N-(3,4-dichlorobenzyl)-3-morpholinosulphinylindole-2-carboxylate (803 mg) in acetone (40 ml) was added a solution of potassium permanganate (528 mg) in water (15 ml). The resulting mixture was stirred for 18 hours. The mixture was poured into water (20 ml) and extracted with diethyl ether, dried (MgSO$_4$) and concentrated to a gum which was purified by column chromatography using iso-hexane:ethyl acetate (3:1) as eluent to give the desired product (681 mg, 82%); NMR d (CDCl$_3$) 1.3 (t, 3H), 3.2–3.2 (m, 4H), 3.7–3.8 (m, 4H), 5.4 (s, 2H), 6.95 (d, 1H), 7.3–7.4 (m, 5H), 8.05 (d, 1H); M/z (+) 499.2 (MH$^+$), 497.3.

EXAMPLE 13

The procedure described above in Example 12 was repeated using the appropriate amine. Thus was obtained the compound described below.

Ethyl N-(3,4-dichlorobenzyl)-3-(1,1-dioxidothiomorpholino)sulphonylindole-2-carboxylate [Ethyl ester Compound 4]
49% yield; NMR d (CDCl$_3$) 1.3 (t, 3H), 3.1–3.2 (m, 4H), 3.9–4.0 (m, 4H), 4.4 (q, 2H), 5.4 (s, 2H), 6.9 (dd, 1H), 7.2–7.4 (m, 5H), 8.0 (d, 1H); M/z (−) 545.2 (M$^+$), 543.1.

EXAMPLE 14

Compound 6

N-(3,4-Dichlorobenzyl)-2-ethoxycarbonylindole-3-sulphonyl chloride (0.12 g), N-methylpiperazine (0.15 ml), triethylamine (0.19 ml) and 4-dimethylaminopyridine (30 mg) were stirred for 4 hours in dichloromethane (2.0 ml). The reaction was washed with water, dried (MgSO$_4$) and concentrated in vacuo. The residue was dissolved in THF/methanol (1:1) and sodium hydroxide (3M, 1.0 ml) was added and the reaction stirred for 16 hours. The reaction was then concentrated in vacuo and the residue dissolved in water. The solution was acidified by dropwise addition of acetic acid, resulting in the precipitation of a white solid which was filtered, washed with water and dried in vacuo to give the desired end product (61 mg, 47%, 2 steps); NMR d (CD$_3$SOCD$_3$) 2.57 (s, 3H), 3.00 (m, 4H), 3.32 (m, 4H), 5.37 (s, 2H), 7.19 (m, 2H), 7.28 (d, 1H), 7.43 (m, 2H), 7.65 (s, 1H), 7.80 (m, 1H); M/z (+) 482 (M$^+$), 236, 215, 196, 159, 142.

EXAMPLE 15

The procedure described in Example 14 above was repeated using the appropriate amines. Thus were obtained the compounds described below.

Compound 7
57% yield (2 steps); NMR d (CD$_3$SOCD$_3$) 2.63 (s, 6H), 3.10 (m, 4H), 5.68 (s, 2H), 7.12–7.26 (m, 3H), 7.44–7.60 (m, 3H), 7.96 (m, 1H), 8.37 (t, 1H); M/z (+) 470 (M$^+$), 214, 158, 141, 123.

Compound 29
61% yield (2 steps); M/z (−) 457 (M$^+$), 455, 413, 411.

Compound 30
30% yield (2 steps); M/z (−) 487 (M$^+$), 485, 443, 441, 399, 397, 355, 353.

Compound 31
23% yield (2 steps), M/z (−) 492 (M−H$^+$), 449, 420, 400, 398, 354, 308, 222.

Compound 32
45% yield (2 steps); M/z (−) 497 (M$^+$), 495, 453, 451.

Compound 33
44% yield (2 steps); M/z (−) 436 (M−CO$_2$$^+$), 434.

Compound 34
40% yield (2 steps); M/z (−) 493 (M$^+$), 449, 447, 340, 338.

Compound 35
49% yield (2 steps); M/z (−) 512 (M$^+$), 510, 468, 466.

Compound 36
60% yield (2 steps); M/z (−) 512 (M$^+$), 510, 468, 466.

Compound 37
52% yield (2 steps); M/z (−) 446 (M−CO$_2$$^+$), 444.

Compound 38
43% yield (2 steps), M/z (−) 443 (M−CO$_2$$^+$), 441.

Compound 39
29% yield (2 steps); M/z (−) 393 (M−CO$_2$$^+$) 391.

Compound 40
54% yield (2 steps); M/z (−) 515 (M$^+$), 513, 471, 469.

Compound 41
34% yield (2 steps); M/z (−) 465 (M−CO$_2$$^+$), 463.

Compound 42
20% yield (2 steps); M/z (−) 473 (M−CO$_2$$^+$), 369, 367.

Compound 43
37% yield (2 steps); M/z (−) 425 (M−CO$_2$$^+$), 423.

Compound 44
5% yield (2 steps); M/z (−) 529 (M$^+$), 527, 485, 483, 355, 353, 274.

Compound 45
17% yield (2 steps); M/z (−) 4663 (M$^+$), 464, 422, 420.

Compound 46
6% yield (2 steps); M/z (−) 451 (M−CO$_2$$^+$), 449, 409, 355, 296, 221.

Compound 47
22% yield (2 steps); M/z (−) 549 (M$^+$), 547, 505, 503, 458, 381, 379, 355, 353.

EXAMPLE 16

Ethyl 3-(2,2-dimethyl-1,3-dioxolane-4-ylmethoxy)indole-2-carboxylate (Precursor to Compounds 70 and 71)

Rhodium acetate dimer (30 mg) was added to a solution of solketal (0.87 ml) and ethyl 3-diazoindole-2-carboxylate (3 mg) in dichloroethane (10 ml), and stirred at 85° C. for 3 hours. The reaction was concentrated in vacuo and the residue purified by column chromatography using a gradient of 0% to 20% ethyl acetate:iso-hexane as eluent to afford the product as a pale yellow solid (435 mg, 97%); NMR d (CD$_3$SOCD$_3$) 1.27–1.38 (m, 9H), 3.88 (m, 1H), 4.11 (m, 3H), 4.30 (q, 2H), (m, 1H), 7.01 (t, 1H), 7.24 (t, 1H), 7.36 (d, 1H), 7.65 (d, 1H), 11.27 (s, 1H); M/z (+) 320.3 (MH$^+$).

EXAMPLE 17

The procedure described in Example 16 above was repeated using the appropriate diazoindole and alcohols. Thus were obtained the compounds described below.

Ethyl 3-[2-(N-acetyl-N-phenylamino)ethoxy]indole-2-carboxylate (Precursor to Compound 76)
75% yield; NMR d (CD$_3$SOCD$_3$) 1.32 (t, 3H), 3.41 (m, 5H), 4.12 (t, 2H), 4.31 (q, 2H), 6.99 (t, 1H), 7.23 (m, 6H), 7.36 (d, 1H), 7.58 (d, 1H), 11.28 (s, 1H); M/z (+) 367.4 (MH$^+$).

Ethyl 3-(3-furylmethoxy)indole-2-carboxylate (Precursor to Compound 77)
47% yield; NMR d (CD$_3$SOCD$_3$) 1.31 (t, 3H), 4.31 (q, 2H), 5.07 (s, 2H), 6.57 (s, 1H), 6.99 (t, 1H), 7.21 (t, 1H), 7.36 (d, 1H), 7.60 (m, 3H); M/z (+) 286.3 (MH$^+$).

Ethyl 3-(cyclohex-2-enylmethoxy)indole-2-carboxylate (Precursor to Compound 78)
90% yield; NMR d (CD$_3$SOCD$_3$) 1.31 (t, 3H), 1.39 (m, 1H), 1.80–2.30 (m, 6H), 4.08 (m, 2H), 4.30 (q, 2H), 5.66 s, 2H), 7.01 (t, 1H), 7.22 (t, 1H), 7.35 (d, 1H), 7.62 (d, 1H), 11.19 (s, 1H); M/z (+) 300.3 (MH$^+$).

Ethyl 3-[4-(hydroxymethyl)cyclohexylmethoxy]indole-2-carboxylate (Precursor to Compound 79)
72% yield; NMR d (CD$_3$SOCD$_3$) 0.80–2.00 (m, 10H), 1.32 (t, 3H), 3.21 (m, 2H), 4.00 (d, 2H), 4.30 (q, 2H), 7.00 (t, 1H), 7.22 (t, 1H), 7.35 (d, 1H), 7.61 (d, 1H), 11.18 (s, 1H); M/z (+) 332.4 (MH$^+$).

Ethyl 3-(4-chlorophenethyloxy)indole-2-carboxylate (Precursor to Compound 80)
81% yield; NMR d (CD$_3$SOCD$_3$) 1.30 (t, 3H), 3.03 (t, 2H), 4.27 (q, 2H), 4.36 (t, 2H), 6.97 (t, 1H), 7.15–7.45 (m, 7H), 11.22 (s, 1H); M/z (+) 344.3 (MH$^+$).

| Precursor to Compd No | Structure | Yield/Properties |
|---|---|---|
| 73 | (indole with 3-O-CH$_2$CH$_2$-N(CH$_3$)-benzoxazol-2-yl; 2-CO$_2$CH$_2$CH$_3$) | 47% yield; M/z (+) 380(MH$^+$). |

-continued

| Precursor to Compd No | Structure | Yield/Properties |
|---|---|---|
| 74 | (structure) | 45% yield; M/z (+) 385(MH+). |
| 75 | (structure) | 53% yield; M/z (+) 347(MH+), 301. |
| 82 | (structure) | 95% yield; NMR d (CDCl$_3$) 1.24(t, 3H), 1.42(t, 3H), 3.60(q, 2H), 3.80(t, 2H), 3.85(s, 3H), 4.38(t, 2H), 4.42(q, 2H), 6.96(dd, 1H), 7.12(d, 1H), 7.20(d, 1H), 8.65(s, 1H); M/z (+) 308(MH+) |
| 83 | (structure) | 65% yield; NMR d (CD$_3$SOCD$_3$) 1.33(t, 3H), 3.70(q, 2H), 3.78(s, 3H), 4.15(t, 2H), 4.32(q, 2H), 4.76(t, 1H), 6.90(dd, 1H), 7.08(d, 1H), 7.26(d, 1H); M/z (+) 280(MH+). |
| 23 | (structure) | 80% yield; NMR d (CDCl$_3$) 1.4(t, 3H), 3.65(t, 1H), 3.8–3.9(m, 2H), 4.4–4.5 (m, 4H), 7.05–7.1(m, 1H), 7.35(d, 2H), 7.7(d, 1H), 8.3(brs, 1H); M/z(+) 250.3 (MH+). |
| 26 | (structure) | 92% yield; NMR d (CDCl$_3$) 1.4(t, 3H), 3.1(t, 1H), 4.4(q, 2H), 4.45(t, 2H), 7.0–7.1(m, 1H), 7.2–7.3(m, 7H), 7.5(d, 1H), 8.35(bs, 1H); M/z (+) 310.3(MH+). |
| 27 | (structure) | 58% yield; NMR d (CDCl$_3$) 1.4(t, 3H), 3.8(s, 3H), 4.4(q, 2H), 4.9(s, 2H), 7.1–7.15(m, 1H), 7.3–7.4(m, 2H), 7.8(d, 1 H), 8.4(brs, 1H); M/z (+) 278.3(MH+). |

| Precursor to Compd No | Structure | Yield/Properties |
|---|---|---|
| 66 | indole with OCH$_2$CH$_2$OCH$_3$ at 3-position and CO$_2$CH$_2$CH$_3$ at 2-position, NH | 94% yield; NMR d (CDCl$_3$) 1.4(t, 3H), 3.5(s, 3H), 3.75(t, 2H), 4.4–4.5(m, 4H), 7.1–7.2(m, 2H), 7.3(d, 2H), 7.8(d, 1H), 8.4(brs, 1H); M/z (+) 264.4(MH$^+$). |
| 67 | indole with OCH$_2$CH$_2$NHCOOC(CH$_3$)$_3$ at 3-position and CO$_2$CH$_2$CH$_3$ at 2-position, NH | 70% yield; NMR d (CDCl$_3$) 1.4–1.5(m, 12H), 3.5–3.6(m, 2H), 4.35(t, 2H), 4.5 (q, 2H), 5.65(brs, 1H), 7.1–7.2(m, 1H), 7.5–7.55(m, 2N), 7.7(d, 1H), 8.4(brs, 1H); M/z (+) 349.4(MH$^+$). |

EXAMPLE 18
Compound 69

To a suspension of ethyl N-(3,4-dichlorobenzyl)-3-[2-(t-butyloxycarbonylamino)ethoxy]indole-2-carboxylate (112 mg) in ethyl acetate (5 ml) was added a saturated solution of HCl in dioxane (2 ml). The mixture was stirred for 18 hours and the resulting solid filtered and dried in vacuo (26 mg, 50%); NMR d (CD$_3$SOCD$_3$) 2.4–2.5 (m, 2H), 4.3–4.4 (m, 2H), 6.9 (d, 1H), 7.1–7.6 (m, 4H), 7.8 (d, 1H), 8.1 (brs, 2H); M/z (−) 379 (M$^+$), 377.

EXAMPLE 19
Ethyl N-(3,4-dichlorobenzyl)-3-(2,3-dihydroxypropoxy) indole-2-carboxylate (Ethyl ester of Compound 71)

Ethyl N-(3,4-dichlorobenzyl)-3-(2,2-dimethyl-1,3-dioxolane-4-ylmethoxy)-indole-2-carboxylate [Compound 70] (15.92 g) was dissolved in tetrahydrofuran (70 ml) and hydrochloric acid (4M, 33 ml), and stirred at ambient temperature for 4 hours. The reaction was concentrated in vacuo, added to water (200 ml) and extracted with ethyl acetate (3×200 ml). The combined organic extracts were dried (MgSO$_4$), and concentrated in vacuo, and the residue purified by column chromatography using 70% ethyl acetate:iso-hexane as eluent, to afford the product as a dark yellow oil that crystallised upon standing to off white crystals (9.37 g, 65%); NMR d (CD$_3$SOCD$_3$)1.27 (t, 3H), 3.50 (m, 2H), 3.83 (m, 1H), 4.08 (m, 1H), 4.20 (m, 1H), 4.27 (q, 2H), 4.58 (t, 1H), 4.88 (d, 1H), 5.73 (s, 2H), 6.88 (d, 1H), 7.15 (t, 1H), 7.33 (m, 2H), 7.54 (m, 2H), 7.82 (d, 1H), M/z (+) 438.3 (MH$^+$).

EXAMPLE 20
t-Butyl N-(3,4-dichlorobenzyl)-3-morpholinoindole-2-carboxylate (t-butyl ester of Compound 72)

Pd$_2$(dba)$_3$ (114 mg), R-BINAP (69 mg), potassium t-butoxide (294 mg), and morpholine (0.209 ml) were added to a solution of t-butyl 3-bromo-N-(3,4-dichlorobenzyl) indole-2-carboxylate (1 g) in de-gassed toluene (6 ml), under an atmosphere of argon. The reaction was stirred and heated at 90° C. for 16 hours then poured into water (50 ml), extracted with ethyl acetate (3×50 ml), and the combined organic extracts were dried (MgSO$_4$) and concentrated in vacuo. The residue was purified by column chromatography using 10% ethyl acetate:iso-hexane as eluent, to afford the product as a yellow oil (325 mg, 33%); NMR d (CD$_3$SOCD$_3$) 3.20 (t, 4H), 3.73 (t, 4H), 5.56 (s, 2H), 6.88 (d, 1H), 7.7 (t, 1H), 7.25 (m, 2H), 7.50 (m, 2H), 7.80 (d, 1H), M/z (+) 461 (MH$^+$), 405.

EXAMPLE 21
N-(3,4-Dichlorobenzyl)-3-morpholinoindole-2-carboxylic acid (Compound 72)

Trifluoroacetic acid (5 ml) was added to a solution of t-butyl N-(3,4-dichlorobenzyl)-3-morpholinoindole-2-carboxylate (293 mg) in dichloromethane (10 ml) and the reaction stirred at ambient temperature overnight. The reaction was concentrated in vacuo and the residue purified by column chromatography using 20% ethyl acetate:iso-hexane as eluent to afford the product as a brown solid (125 mg, 30%); NMR d (CD$_3$SOCD$_3$) 3.10 (t, 4H), 3.83 (t, 4H), 5.36 (s, 2H), 7.01 (t, 1H), 7.12 (m, 2H), 7.46 (m, 2H), 7.58 (m, 2H), M/z(−) 404.2 (M−H$^+$).

EXAMPLE 22
Compound 48

Acetic anhydride (0.4 g) was added to a stirred solution of N-(3,4-dichlorobenzyl)-2-carboxy-3-indoleacetic acid (0.1 g) in dry DCM (5 mls) under an inert atmosphere and heated to 50° C. for 4 hours. The reaction was cooled, concentrated in vacuo and toluene added before reducing in vacuo again. The resultant yellow solid was dissolved in DCM under an inert atmosphere before morpholine (0.6 mls) was added and the reaction was stirred for 48 hours at ambient temperature. Combined organic extracts were washed with aqueous hydrochloric acid (2.0 M, 5 ml), water and saturated aqueous sodium chloride solution before concentration in vacuo. The residue was dissolved in saturated aqueous sodium hydrogen orthophosphate and acidified by the addition of aqueous hydrochloric acid (2.0 M, 5 ml) causing the precipitation of the product as a light brown solid. (0.098 g, 83%); NMR d (CD$_3$SOCD$_3$) 3.51 (brs, 2H), 3.60 (M, 4H), 3.71 (brs, 2H), 4.23 (s, 2H), 5.88 (s, 2H), 6.99 (d, 1H), 7.19 (t, 1H), 7.32–7.40 (m, 2H), 7.56–7.63 (m, 2H), 7.78 (d, 1H); M/z (−) 445 (M−H$^+$).

EXAMPLE 23

The procedure described in Example 22 above was repeated using the appropriate amines. Thus were obtained the compounds described below.

Compound 49

69% yield; NMR d (CD$_3$SOCD$_3$) 3.11 (dd, 2H), 3.38 (t, 2H), 3.96 (s, 2H), 5.78 (s, 2H), 6.91 (dd, 1H), 7.12 (t, 1H), 7.24–7.35 (m, 2H), 7.44–7.53 (m, 2H), 7.72 (d, 1H), 8.02 (M, 1H); M/z (−) 419 (M−H$^+$).

Compound 52

44% yield; M/z (−) 433 (M−H$^+$).

Compound 53
  32% yield; M/z (−) 469 (M−H$^+$).
Compound 54
  69% yield; M/z (−) 486 (M−H$^+$).
Compound 55
  42% yield; M/z (−) 491 (M−H$^+$).
Compound 56
  38% yield; M/z (−) 433 (M−H$^+$).
Compound 57
  58% yield; M/z (−) 459 (M−H$^+$).
Compound 58
  12% yield; M/z (−) 544 (M−H$^+$).
Compound 59
  52% yield; M/z (−) 459 (M−H$^+$).
Compound 60
  21% yield; M/z (−) 515 (M−H$^+$).
Compound 61
  25% yield; M/z (−) 558 (M−H$^+$).
Compound 62
  18% yield; M/z (−) 489 (M−H$^+$).
Compound 63
  19% yield; M/z (−) 509 (M−H$^+$).
Compound 64
  10% yield; M/z (−) 495 (M−H$^+$).
Compound 65
  18% yield; M/z (−) 469 (M−H$^+$).

EXAMPLE 24

Compound 8

3,5-Dimethylisoxazole-4-sulphonyl chloride (0.097 g) in dichloromethane (2 ml) was added to a stirred solution of ethyl 3-amino-N-(3,4-dichlorobenzyl)indole-2-carboxylate (0.15 g) in dichloromethane (3 ml). Pyridine (0.036 g) was added and the reaction was stirred for 16 hours at ambient temperature. The reaction mixture was washed with aqueous citric acid (1.0M, 4 ml), saturated aqueous sodium hydrogencarbonate solution and water and concentrated in vacuo. The residue was dissolved in THF (5 ml) and LIOH (2M, 3 ml) added and the reaction stirred for 16 hours. The reaction was then concentrated in vacuo and the residue dissolved in water. The solution was acidified by dropwise addition of acetic acid, resulting in the precipitation of a white solid which was filtered, washed with water and dried in vacuo to give the desired end product as a white solid. (75 mg, 37%, 2 steps); NMR d (CD$_3$SOCD$_3$) 2.00 (s, 3H), 2.07 (s, 3H), 5.74 (s, 2H), 6.93 (dd, 1H), 7.17 (t, 1H), 7.24 (d, 1H), 7.34 (t, 1H), 7.55 (dd, 2H), 7.66 (d, 1H), 9.72 (brs, 1H); M/z (−) 492 (M−H$^+$).

EXAMPLE 25

The procedure described in Example 24 above was repeated using the appropriate acid chloride. Thus were obtained the compounds described below.

Compound 9
  48% yield (2 steps), NMR d (CD$_3$SOCD$_3$) 2.00 (s, 3H), 2.14 (s, 3H), 5.71 (s, 2H), 6.77 (d, 1H), 7.12 (t, 1H), 7.26–7.37 (m, 2H), 7.45 (d, 1H), 7.52 (d, 1H), 7.63 (d, 1H), 9.58 (brs, 1H), 12.39 (s, 1H); M/z (−) 551 (M−H$^+$).
Compound 10
  66% yield (2 steps); NMR d (CD$_3$SOCD$_3$) 3.56 (s, 3H), 5.71 (s, 2H), 6.82 (dd, 1H), 7.07 (t, 1H), 7.21–7.30 (m, 2H), 7.45–7.55 (m, 3H), 7.66–7.73 (m, 2H), 9.10 (s, 1H); M/z (−) 477 (M−H$^+$).
Compound 11
  69% yield (2 steps); NMR d (CD$_3$SOCD$_3$) 4.10 (s, 2H), 5.79 (s, 2H), 6.93 (dd, 1H), 7.18 (t, 1H), 7.29–7.36 (m, 2H), 7.50–7.59 (m, 2H), 7.81 (d, 1H); M/z (−) 455 (M−H$^+$).
Compound 12
  14% yield (2 steps), NMR d (CD$_3$SOCD$_3$) 1.94 (s, 3H), 3.61 (s, 3H), 5.70 (s, 2H), 6.84 (dd, 1H), 7.12 (t, 1H), 7.2 7–7.34 (m, 2H), 7.52 (t, 2H), 7.61 (d, 1H), 9.28 (brs, 1H); M/z (−) 525, 527, 529 ) (M−H$^+$).
Compound 13
  79% yield (2 steps); NMR d (CD$_3$SOCD$_3$) 3.49 (s, 3H), 5.68 (s, 2H), 6.79 (dd, 1H), 7.13 (t, 1H), 7.19 (d, 1H), 7.30 (t, 1H), 7.50–7.56 (m, 2H), 7.59–7.77 (m, 3H), 7.91 (t, 1H), 8.23 (d, 1H), 8.87 (brs, 1H); M/z (−) 551 (M−H$^+$).
Compound 14
  36% yield (2 steps); NMR d (CD$_3$SOCD$_3$) 3.46 (s, 2H), 5.79 (s, 2H), 6.91 (dd, 1H), 7.09 (t, 1H), 7.25–7.35 (m, 2H), 7.50–7.58 (m, 2H), 7.62 (d, 1H), 9.89 (brs, 1H),
Compound 15
  90% yield (2 steps); NMR d (CD$_3$SOCD$_3$) 2.10 (s, 3H), 2.67 (m, 2H), 2.76 (m, 2H), 5.79 (s, 2H), 6.92 (dd, 1H), 7.10 (t, 1H), 7.28–7.33 (m, 2H) 7.50–7.56 (m, 2H), 7.61 (d, 1H), 9.67 (s, 1H); M/z (−) 435 (M−H$^+$).
Compound 16
  73% yield (2 steps); NMR d (CD$_3$SOCD$_3$) 3.96 (s, 2H), 5.79 (s, 2H), 6.90 (s, 1H), 6.94–7.13 (m, 3H), 7.26–7.34 (m, 3H), 7.38 (d, 1H), 7.48–7.59 (m, 3H), 9.86 (s, 1H), 13.36 (brs, 1H); M/z (−) 457 (M−H$^+$),
Compound 17
  53% yield (2 steps); NMR d (CD$_3$SOCD$_3$) 1.36 (d, 3H), 4.20 (m, 1H), 5.79 (s, 2H), 6.00 (d, 1H), 6.88 (dd, 1H), 7.07 (t, 1H), 7.28–7.35 (m, 2H), 7.50–7.56 (m, 2H), 7.99 (d, 1H), 10.21 (brs, 1H); M/z (−) 405 (M−H$^+$).
Compound 18
  73% yield (2 steps); NMR d (CD$_3$SOCD$_3$) 3.83 (s, 6H), 5.81 (s, 2H), 6.95 (dd, 1H), 7.06–7.17 (m, 2H), 7.30–7.37 (m, 2H), 7.51–7.61 (m, 3H), 7.66 (dd, 1H), 7.75 (d, 1H), 10.08 (brs, 1H); M/z (−) 497 (M−H$^+$).
Compound 19
  66% yield (2 steps); NMR d (CD$_3$SOCD$_3$) 2.04 (s, 3H), 5.68 (s, 2H), 6.60 (dd, 1H), 7.12 (d, 1H), 7.20 (d, 1H), 7.28 (t, 1H), 7.40 (d, 2H), 7.47 (d, 2H), 7.62 (d, 2H), 7.72 (d, 1H), 9.13 (s, 1H), 10.27 (s, 1H); M/z (−) 530 (M−H$^+$).
Compound 20
  47% yield (2 steps); NMR d (CD$_3$SOCD$_3$) 5.78 (s, 2H), 6.86 (dd, 1H), 7.10–7.18 (m, 3H), 7.21 (d, 1H), 7.31 (t, 1H), 7.54 (dd, 1H), 7.63 (d, 1H), 9.80 (brs, 1H); M/z (−) 517 (M−H$^+$). 515, 513.
Compound 22
  40% yield (2 steps): NMR d (CD$_3$SOCD$_3$) 4.69 (s, 2H), 5.76 (s, 2H), 6.84 (dd, 1H), 7.14 (t, 1H), 7.23–7.40 (m, 3H), 7.46–7.67 (m, 3H), 7.85 (d, 1H), 10.13 (brs, 1H); M/z (−) 5.46 (M−H$^+$),

EXAMPLE 26

Methyl Ester of Compound 1

To a solution of methyl 3-amino-N-(3,4-dichlorobenzyl) indole-2-carboxylate (253 mg) in tetrahydrofuran (8 ml) was added triethylamine (0.15 ml) followed by a solution of 3-chlorobenzoyl chloride (153 mg) in tetrahydrofuran (2 ml). The resulting mixture was stirred at room temperature for 4 hours. The mixture was partitioned between water (10 ml) and ethyl acetate (20 ml). The organic layer was dried (MgSO$_4$) and concentrated in vacuo. The residue was purified by column chromatography using ixo-hexane: 20% ethyl acetate as eluent to give the product (259 mg, 74%); NMR d (CDCl$_3$) 3.9 (s, 3H), 5.7 (s, 2H), 6.8 (d, 1H), 7.2–7.6 (m, 7H), 7.9 (d, 1H), 8.05 (s, 1H), 8.3 (d, 1H), 10.1 (brs, 1H): M/z (−) 487.1 (M$^+$), 485.0.

EXAMPLE 27

The procedure described in Example 26 above was repeated using the appropriate acid chloride. Thus was obtained the compound described below.

Methyl Ester of Compound 2

37% yield; NMR d (CDCl$_3$) 2.95 (s, 3H), 3.95 (s, 3H), 5.7 (s, 2H), 6.8 (dd, 1H), 7.1–7.5 (m, 4H), 7.7 (s, 1H), 8.15 (d, 1H), M/z (−) 427.3 (M$^+$), 425.3.

EXAMPLE 28

Ethyl N-(3,4-dichlorobenzyl)-3-(tetrahydrofurfurylcarbamoyl)indole-2-carboxylate (Ethyl ester of Compound 68)

To a stirred solution of ethyl N-(3,4-dichlorobenzyl)-2-ethoxycarbonylindole-3-carboxylic acid (100 mg) in dichloromethane (4 ml) at ambient temperature, under argon, was added DMF (1 drop) and oxalyl chloride in dichloromethane (2M, 153 μl). The reaction was stirred at ambient temperature for 7 hours, then concentrated in vacuo and dissolved in dichloromethane (4 ml). Tetrahydrofurfurylamine (53 μl) was added, followed by triethylamine (71 μl) and the reaction stirred under argon for 16 hours. The reaction was diluted with dichloromethane (30 ml), washed with HCl (2M, 30 ml) and water (30 ml), dried (MgSO$_4$) and concentrated in vacuo to give a crude residue which was purified by column chromatography, using ethyl acetate:iso-hexane as eluent (gradient 10/90–50/50), to give the product as an off-white solid (57 mg, 47%); M/z (+) 475.3 (MH$^+$),

EXAMPLE 29

Ethyl N-(3,4-dichlorobenzyl)-3-(1,1-dioxidotetrahydrothiophene-3-carbamoyl)indole-2-carboxylate (Ethyl ester of Compound 81)

Ethyl N-(3,4-dichlorobenzyl)-2-ethoxycarbonylindole-3-carboxylic acid (104 mg), 1-(3-dimethylaminopropyl)-3-ethylcarbodiimide hydrochloride (76 mg), 3-aminotetrahydrothiophene 1,1-dioxide (36 mg) and 4-dimethylaminopyridine (5 mg) in dichloromethane (10 ml) were stirred at ambient temperature under argon for 16 hours. The crude reaction mixture was purified by column chromatography using ethyl acetate:iso-hexane as eluent (gradient 0/100–75/25), to give the product as a white solid (32 mg, 24%), M/z (+) 509.4 (MH$^+$).

EXAMPLE 30

The procedure described in Example 29 above was repeated using the appropriate amines. Thus were obtained the compounds described below.

Ethyl N-(3,4-dichlorobenzyl)-3-(1,1-dioxidothiomorpholinocarbonyl)indole-2-carboxylate (Ethyl ester of Compound 84)

48% yield; M/z (+) 509.1 (MH$^+$).

Ethyl N-(3,4-dichlorobenzyl)-3-(3,5-dimethylisoxazol-4-ylmethylcarbamoyl)indole-2-carboxylate (Ethyl ester of Compound 85)

40% yield; M/z(+) 500.1 (MH$^+$).

EXAMPLE 31

Ethyl (Z)-N-(3,4-dichlorobenzyl)-2-ethoxycarbonylindole-3-acrylic acid (Ethyl ester of Compound 50)

Malonic acid (106 mg) and piperidine (1 drop) were added to a solution of ethyl 3-formyl-N-(3,4-dichlorobenzyl)indole-2-carboxylate (315 mg) in pyridine (5 ml) and the reaction stirred at 100° C. overnight. The reaction was concentrated in vacuo and the residue dissolved in ethyl acetate (30 ml), washed with HCl (2M, 30 ml) and water (30 ml), dried (MgSO$_4$) and concentrated in vacuo to give the crude product which was triturated with a mixture of dichloromethane, ethyl acetate and hexane to give the product as a tan coloured solid (68 mg, 19%); NMR d (CD$_3$SOCD$_3$) 1.25 (t, 3H), 4.35 (q, 2H), 5.80 (s, 2H), 6.55 (d, 1H), 6.90 (m, 1H), 7.25–7.45 (m, 3H), 7.50 (m, 1H), 7.60 (m, 1H), 8.05 (m, 1H), 8.35 (d, 1H) 12.24 (s, 1H); M/(−) 416.4 (M−H$^+$).

EXAMPLE 32

Biological Assays for hMCP-1 Antagonists

The following biological test methods, data and Examples serve to illustrate the present invention.

Abbreviations

| | |
|---|---|
| ATCC | American Type Culture Collection, Rockville, USA. |
| BCA | Bicinchroninic acid, (used with copper sulphate to assay protein) |
| BSA | Bovine Serum Albumin |
| DMEM | Dulbecco's modified Eagle's medium |
| EGTA | Ethylenebis(oxyethylenenitrilo)tetraacetic acid |
| FCS | Foetal calf serum |
| HEPES | (N-[2-Hydroxyethyl]piperazine-N'-[2-ethanesulphonic acid]) |
| HBSS | Hank's Balanced Salt Solution |
| hMCP-1 | Human Monocyte Chemoattractant Protein-1 |
| PBS | Phosphate buffered saline |
| PCR | Polymerase chain reaction |

AMPLITAQ™, available from Perkin-Elmer Cetus, is used as the source of thermostable DNA polymerase.

Binding Buffer is 50 mM HEPES, 1 mM CaCl$_2$, 5 mM MgCl$_2$, 0.5% foetal calf serum, adjusted to pH 7.2 with 1 M NaOH.

Non-Essential Amino Acids (100×concentrate) is: L-Alanine, 890 mg/l; L-Asparagine, 1320 mg/l; L-Aspartic acid, 1330 mg/l; L-Glutamic acid, 1470 mg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt); 5000 units/ml; Streptomycin sulphate, 5000 μg/ml.

Human monocytic cell line THP-1 cells are available from ATCC, accession number ATCC TIB-202.

Hank's Balanced Salt Solution (HBSS) was obtained from Gibco; see Proc. Soc. Exp. Biol. Med., 1949, 71, 196.

Synthetic cell culture medium, RPMl 1640 was obtained from Gibco; it contains inorganic salts [Ca(NO$_3$)$_2$, 4H$_2$O 100 mg/l; KCl 400 mg/l; MgSO$_4$.7H$_2$O 100 mg/l; NaCl 6000 mg/l; NaHCO$_3$2000 mg/l & NA$_2$HPO$_4$ (anhyd) 800 mg/l], D-Glucose 2000 mg/l, reduced glutathione 1 mg/l, amino acids and vitamins.

FURA-2/AM is 1-[2-(5-carboxyoxazol-2-yl)-6-aminobenzofuran-5-oxy]-2-(2'-amino-5'-methylphenoxy)-ethane-N,N,N',N'-tetraacetic acid pentaacetoxymethyl ester and was obtained from Molecular Probes, Eugene. Ore. USA.

Blood Sedimentation Buffer contains 8.5 g/l NaCl and 10 g/l hydroxyethyl cellulose.

Lysis Buffer is 0.15M NH$_4$Cl$^+$, 10 mM KHCO$_3$, 1 mM EDTA

Whole Cell Binding Buffer is 50 mM HEPES. 1 mM CaCl$_2$, 5 mM MgCl$_2$, 0.5% BSA, 0.01% NaN$_3$, adjusted to pH 7.2 with 1M NaOH.

Wash buffer is 50 mM HEPES. 1 mM CaCl$_2$, 5 mM MgCl$_2$, 0.5% heat inactivated FCS. 0.5MNaCl adjusted to pH7.2 with 1M NaOH.

General molecular biology procedures can be followed from any of the methods described in "Molecular Cloning—A Laboratory Manual" Second Edition, Sambrook, Fritsch and Maniatis (Cold Spring Harbor Laboratory, 1989).

i) Cloning and Expression of hMCP-1 Receptor

The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad Sci. USA*. 91, 2752). The resulting PCR products were cloned into vector PCR-II™ (In Vitrogen, San Diego, Calif.). Error free CCR2B cDNA was subcloned as a Hind III-Not I fragment into the eukaryotic expression vector pCDNA3 (In Vitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6, 134). CHO-K1 clone 7 (CHO-CCR2B) was identified as the highest MCP-1 receptor B expressor.

ii) Preparation of Membrane Fragments

CHO-CCR2B cells were grown in DMEM supplemented with 10% foetal calf serum. 2 mM glutamine. 1× Non-Essential Amino Acids, 1× Hypoxanthine and Thymidine Supplement and Penicillin-Streptomycin (at 50 μg streptomycin/ml, Gibco BRL). Membrane fragments were prepared using cell lysis/differential centrifugation methods as described previously (Siciliano et al., 1990, *J. Biol. Chem.*, 265, 19658). Protein concentration was estimated by BCA protein assay (Pierce, Rockford, Ill.) according to the manufacturer's instructions.

iii) Assay $^{125}$I MCP-1 was prepared using Bolton and Hunter conjugation (Bolton et al. 1973. *Biochem. J.*, 133, 529, Amersham International plc]. Equilibrium binding assays were carried out using the method of Ernst et al., 1994, *J. Immunol.*, 152, 3541. Briefly, varying amounts of $^{125}$I-labeled MCP-1 were added to 7 μg of purified CHO-CCR2B cell membranes in 100 μl of Binding Buffer. After 1 hour incubation at room temperature the binding reaction mixtures were filtered and washed 5 times through a plate washer (Brandel MLR-96T Cell Harvester) using ice cold Binding Buffer. Filter mats (Brandel GF/B) were pre-soaked for 60 minutes in 0.3% polyethylenimine prior to use. Following filtration individual filters were separated into 3.5 ml tubes (Sarstedt No. 55,484) and bound $^{125}$I-labeled MCP-1 was determined (LKB 1277 Gammamaster). Cold competition studies were performed as above using 100 pM $^{125}$I-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B receptor was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 μl) were tested in competition with 100 pM labelled MCP-1 over a concentration range (0.01–50 μM) in duplicate using eight point dose-response curves and $IC_{50}$ concentrations were calculated.

Compounds tested of the present invention had $IC_{50}$ values of 50 μM or less in the hMCP-1 receptor binding assay described herein. For example Compound 81 had an $IC_{50}$ of 6.86 μM.

b) MCP-1 Mediated Calcium Flux in THP-1 Cells

The human monocytic cell line THP-1 was grown in a synthetic cell culture medium RPMI 1640 supplemented with 10% foetal calf serum. 6 mM glutamine and Penicillin-Streptomycin (at 50 μg streptomycin/mil, Gibco BRL). THP-1 cells were washed in HBSS (lacking $Ca^{2+}$ and $Mg^{2+}$)+1 mg/ml BSA and resuspended in the same buffer at a density of 3×10$^6$ cells/ml. The cells were then loaded with 1 mM FURA-2/AM for 30 min at 37° C., washed twice in HBSS, and resuspended at 1×10$^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA. 1 mM $MgCl_2$ and 2 mM $CaCl_2$. The cuvette was placed in a fluorescence spectrophotometer (Perkin Elmer, Norwalk, Conn.) and pre-incubated for 4 min at 37° C. with stirring. Fluorescence was recorded over 70 sec and cells were stimulated by addition of hMCP-1 to the cuvette after 10 sec. [$Ca^{2+}$]i was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic [$Ca^{2+}$] according to the equation:

$$[Ca^{2+}]i = K_d \frac{(R-R\min)}{(R\max-R)}(Sf2/Sb2)$$

where the $K_d$ for FURA-2 $Ca^{2+}$ complex at 37° C. was taken to be 224 nm. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in [$Ca^{2+}$]$_i$ in a specific and dose dependent manner. Dose response curves indicated an approximate $EC_{50}$ of 2 nm. Test compounds dissolved in DMSO (10 μl) were assayed for inhibition of calcium release by adding them to the cell suspension 10 sec prior to ligand addition and measuring the reduction in the transient rise in [$Ca^{2+}$]i. Test compounds were also checked for lack of agonist activity by addition in place of hMCP-1.

c) hMCP-1 and RANTES Mediated Chemotaxis

In vitro chemotaxis assays were performed using the human monocytic cell line THP-1. Cell migration through polycarbonate membranes was measured by enumerating those passing through either directly by Coulter counting or indirectly by use of a colourimetric viability assay measuring the cleavage of a tetrazolium salt by the mitochondrial respirator chain (Scudiero D. A., et al. 1988, *Cancer Res.*, 48, 4827–4833).

Chemoattractants were introduced into a 96-well microtitre plate which forms the lower well of a chemotaxis chamber fitted with a PVP-free 5 μm poresize polycarbonate adhesive framed filter membrane (NeuroProbe MB series, Cabin John, Md. 20818, USA) according to the manufacturer's instructions. The chemoattractant was diluted as appropriate in synthetic cell culture medium. RPMI 1640 (Gibco) or supplemented with 2 mM glutamine and 0.50% BSA, or alternatively with HBSS with $Ca^{2+}$ and $Mg^{2+}$ without Phenol Red (Gibco) plus 0.1% BSA. Each dilution was degassed under vacuum for 30 min and was placed (400 µl) in the lower wells of the chamber and THP-1 cells ($5 \times 10^5$ in 100 µl RPMI 1640+0.5% BSA) were incubated in each well of the upper chamber. For the inhibition of chemotaxis the chemoattractant was kept at a constant submaximal concentration determined previously (1 nM MCP-1) and added to the lower well together with the test compounds dissolved in DMSO (final DMSO concentration<0.05% v/v) at varying concentrations. The chamber was incubated for 2 h at 37° C. under 5% $CO_2$. The medium was removed from the upper wells which were then washed out with 200 µl physiological saline before opening the chamber, wiping dry the membrane surface and centrifuging the 96-well plate at 600 g for 5 min to harvest the cells. Supernatant (150 µl) was aspirated and 10 µl of cell proliferation reagent, WST-1, {4-[3-(4-iodophenyl)-2-(4-nitrophenyl)-2H-5-tetrazolio]-1,3-phenyl disulfonate} plus an electron coupling reagent (Boehringer Mannheim. Cat, no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated, hMCP-1 induced concentration dependent cell migration with a characteristic biphasic response, maximal 0.5–1.0 nm.

In an alternative form of the above assay, fluorescently tagged cells can be used in order to assist in end point detection. In this case, the THP-1 cells used are fluorescently tagged by incubation in the presence of 5 mM Calcein AM (Glycine, N,N'-[[3',6'-bis(acetyloxy)-3-oxospiro[isobenzofuran-1(3H),9'-[9H]xanthene]-2',7'-diyl]bis(methylene)]bis[N-[2-[(acetyloxy)methoxy]-2-oxoethyl]]-bis[(acetyloxy)methyl]ester; Molecular Probes) for 45 minutes in the dark. Cells are harvested by centrifugation and resuspended in HBSS (without Phenol Red) with $Ca^{2+}$, $Mg^{2+}$ and 0.1% BSA. 50 µl ($2 \times 10^5$ cells) of the cell suspension are placed on the filter above each well and, as above, the unit is incubated at 37° C. for 2 hours under 5% $CO_2$. At the end of the incubation, cells are washed off the upper face of the filter with phosphate buffered saline, the filter removed from the plate and the number of cells attracted to either the underside of the filter or the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and $IC_{50}$ of compounds under test and significance tests can be calculated. In addition to MCP-1 induced chemotaxis, this alternative form of the assay was also used to measure inhibition of RANTES (2 nM) induced chemotaxis.

d) Binding to Human Peripheral Blood Mononuclear Cells (PBMCs)
i) Preparation of Human PBMCs
Fresh human blood (200 ml) was obtained from volunteer donors, collected into sodium citrate anticoagulant to give a final concentration of 0.38%. The blood was mixed with Sedimentation Buffer and incubated at 37° C. for 20 minutes. The supernatant was collected and centrifuged at 1700 rpm for 5 minutes (Sorvall RT6000D). The pellet obtained was resuspended in 20 ml RPMI/BSA (1 mg/ml) and $4 \times 5$ mls of cells were carefully layered over $4 \times 5$ mls of Lymphoprepä (Nycomed) in 15 ml centrifuge tubes. Tubes were spun at 1700 rpm for 30 minutes (Sorvall RT6000D) and the resultant layer of cells was removed and transferred to 50 ml Falcon tubes. The cells were washed twice in Lysis Buffer to remove any remaining red blood cells followed by 2 washes in RPMI/BSA. Cells were resuspended in 5 mls of Binding Buffer. Cell number was measured on a Coulter counter and additional binding buffer was added to give a final concentration of $1.25 \times 10^7$ PBMCs/ml.

ii) Assay

[$^{125}$I]MCP-1 was prepared using Bolton and Hunter conjugation (Bolton et al., 1973, *Biochem. J.*, 133, 529; Amersham International plc]. Equilibrium binding assays were carried out using the method of Ernst et al., 1994, *J. Immunol.*, 152, 3541. Briefly, 50 µl of $^{125}$I-labeled MCP-1 (final concentration 100 pM) was added to 40 µl ($5 \times 10^5$ cells) of cell suspension in a 96 well plate. Compounds, diluted in Whole Cell Binding Buffer from a stock solution of 10 mM in DMSO were added in a final volume of 5 µl to maintain a constant DMSO concentration in the assay of 5%. Total binding was determined in the absence of compound. Non-specific binding was defined by the addition of 5 µl cold MCP-1 to give a final assay concentration of 100 nM. Assay wells were made up to a final volume of 100 µl with Whole Cell Binding Buffer and the plates sealed. Following incubation at 37° C. for 60 minutes the binding reaction mixtures were filtered and washed for 10 seconds using ice cold Wash Buffer using a plate washer (Brandel MLR-96T Cell Harvester). Filter mats (Brandel GF/B) were pre-soaked for 60 minutes in 0.3% polyethylenimine plus 0.2% BSA prior to use. Following filtration individual filters were separated into 3.5 ml tubes (Sarstedt No. 55.484) and bound $^{125}$I-labeled MCP-1 was determined (LKB 1277 Gammamaster).

Test compound potency was determined by assay in duplicate using six point dose-response curves and $IC_{50}$ concentrations were determined.

For example, using this method, compound No. 14 in Table I showed an $IC_{50}$ of 11.4 µM in the hMCP-1 chemotaxis assay and compound No.23 in Table 1 showed an $IC_{50}$ of 2.95 µM in the RANTES chemotaxis assay.

No physiologically unacceptable toxicity was observed at the effective dose for compounds tested of the present invention.

EXAMPLE 33

Pharmaceutical Compositions

The following Example illustrates, but is not intended to limit, pharmaceutical dosage forms of the invention as defined herein (the active ingredient being termed "Compound X"), for therapeutic or prophylactic use in humans:

(a)

| Tablet I | mg/tablet |
| --- | --- |
| Compound X. | 100 |
| Lactose Ph. Eur | 182.75 |
| Croscarmellose sodium | 12.0 |
| Maize starch paste (5% w/v paste) | 2.25 |
| Magnesium stearate | 3.0 |

(b)

| Tablet II | mg/tablet |
| --- | --- |
| Compound X | 50 |
| Lactose Ph. Eur | 223.75 |
| Croscarmellose sodium | 6.0 |
| Maize starch | 15.0 |
| Polyvinylpyrrolidone | 2.25 |

-continued

| (5% w/v paste) | |
|---|---|
| Magnesium stearate | 3.0 |

(c)

| Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

(d)

| Capsule | mg/capsule |
|---|---|
| Compound X | 10 |
| Lactose Ph. Eur | 488.5 |
| Magnesium | 1.5 |

(e)

| Injection I | (50 mg/ml) |
|---|---|
| Compound X | 5.0% w/v |
| 1 M Sodium hydroxide solution | 15.0% v/v |
| 0.1 M Hydrochloric acid | to adjust pH to 7.6 |
| Polyethylene glycol 400 | 4.5% w/v |
| Water for injection | to 100% |

(f)

| Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection | to 100% |

(g)

| Injection III | (1 mg/ml. buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

(h)

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

(i)

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j)

| Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

-continued (k)

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l)

| Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note:
Compound X in the above formulation may comprise a compound illustrated in Examples herein. The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleateand soya lecithin may be replaced by an alternative suspending agent such as sorbitan monooleate, sorbitan sesquioleate, polysorbate 80, polyglycerol oleate or oleic acid.

What is claimed is:

1. A method for treating 'rheumatoid arthritis, glomerular nephritides, lung fibrosis, restenosis, asthma, atherosclerosis, psoriasis, delayed-type hypersensitivity reactions of the skin, inflammatory bowel disease, multiple sclerosis, inflammation resulting from brain trauma, stroke, ischemia, myocardial infarction and transplant rejection' comprising inhibiting monocyte chemoattractant protein-1 and/or RANTES-induced chemotaxis, said method comprising administering to a patient in need thereof an effective amount of a compound of formula (I)

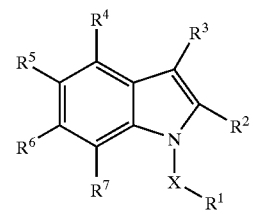

(I)

or a pharmaceutically acceptable salt or ester thereof; wherein

X is $CH_2$ or $SO_2$;

$R^1$ is an optionally substituted aryl ring;

$R^2$ is carboxy, cyano, $-C(O)CH_2OH$, $-CONHR^8$, $-SO_2NHR^9$, or $SO_3H$, where $R^8$ is selected from hydrogen, alkyl, aryl, cyano, hydroxy, $-SO_2R^{12}$ where $R^{12}$ is alkyl, aryl, or haloalkyl, or $R^8$ is a group $-(CHR^{13})_r-COOH$ where r is an integer of 1–3 and each $R^{13}$ group is independently selected from hydrogen or alkyl; $R^9$ is hydrogen, alkyl, or optionally substituted aryl, or a group $COR^{14}$ where $R^{14}$ is alkyl, aryl, or haloalkyl; and $R^{10}$ and $R^{11}$ are independently selected from hydrogen or alkyl, particularly $C_{1-4}$ alkyl;

$R^3$ is a group $OR^{15}$, $S(O)_qR^{15}$, $NHCOR^{16}$, $NHSO_2R^{16}$, $(CH_2)_sCOOH$, $(CH_2)_tCONR^{17}R^{18}$, $NR^{17}R^{18}$, $SO_2NR^{17}R^{18}$ or optionally substituted alkenyl, where q is 0, 1 or 2, s is 0 or an integer of from 1 to 4, t is 0 or an integer of from 1 to 4, $R^{15}$ is a substituted cycloalkyl group or an alkyl group substituted with one or more groups selected from halogen, hydroxy, cyano, amino, mono- or di-alkylamino, $C_{1-4}$ alkoxy, carboxy, sulphonamido, $CONH_2$, morpholino, pyridyl, pyrimidinyl, phenyl optionally substituted by halogen, carboxy, alkoxy, carbamoyl, acyl groups, or hydroxyalkyl wherein the alkyl group in the hydroxyalkyl moiety includes at least two carbon atoms, $R^{16}$ is optionally substituted alkyl or optionally substituted aryl, and $R^{17}$ and $R^{18}$ are independently selected from hydrogen, optionally substituted alkyl, and optionally substituted aryl, with the proviso that at least one of $R^{17}$ or $R^{18}$ is other than hydrogen; and $R^4$ is selected from hydrogen, hydroxyl, halo, alkoxy, aryloxy, araalkyl, carboxyalkyl; and $R^5$, $R^6$, and $R^7$ are independently selected from hydrogen, hydroxyl, halo, alkoxy, or an optionally substituted hydrocarbyl group.

2. A method according to claim 1, wherein $R^3$ is $OR^{15}$, $S(O)_qR^{15}$, $NHCOR^{16}$, $NHSO_2R^{16}$, or $SO_2NR^{17}R^{18}$, where q, $R^{15}$, $R^{16}$, $R^{17}$ and $R^{18}$ are as defined in claim 1.

3. A method according to claim 1, wherein $R^3$ is a group of formula $-O(CH_2)_a[(CHOH)(CH_2)_b]_dCH_2OH$, where a is 0 or an integer of from 1 to 4, b is 0 or an integer of from 1 to 3, and d is 0 or 1.

4. A method according to claim 1, wherein $R^1$ is 3,4-dichlorophenyl, 3-fluoro-4-chlorophenyl, or 3-chloro-4-fluorophenyl or 2,3-dichloropyrid-5-yl.

5. A method according to claim 1, wherein X is $CH_2$.

6. A pharmaceutical composition comprising a compound of formula (I) as defined in claim 1 subject to the following provisos:
(i) when $R^2$ is carboxy or a salt or amide thereof, at least three of $R^4$, $R^5$, $R^6$, and $R^7$ are hydrogen, and $R^3$ is $S(O)_qR^{15}$, then $R^{15}$ is other than $C_{1-4}$ alkyl substituted by carboxy or an ester or amide derivative thereof;
(ii) when $R^3$ is a group $NHCOR^{16}$, then $R^{16}$ is optionally substituted alkyl; and
(iii) when $R^3$ is a group $SR^{15}$, where $R^{15}$ is 2-quinolylmethyl, $R^2$ is COOH or an ethyl ester thereof, each of $R^4$, $R^5$, and $R^7$ are hydrogen, and $R^1$ is 4-chlorophenyl, then $R^6$ is other than 2-quinolylmethyl;
in combination with a pharmaceutically acceptable carrier.

7. A compound of formula (I)

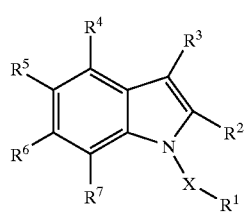

(I)

or a pharmaceutically acceptable salt or ester thereof; wherein

X is $CH_2$ or $SO_2$;

$R^1$ is an optionally substituted aryl ring;

$R^2$ is carboxy, cyano, $-C(O)CH_2OH$, $-CONHR^8$, $-SO_2NHR^9$, $SO_3H$, where $R^8$ is selected from hydrogen, alkyl, aryl, cyano, hydroxy, $-SO_2R^{12}$ where $R^{12}$ is alkyl, aryl, or haloalkyl, or $R^8$ is a group $-(CHR^{13})_r-COOH$ where r is an integer of 1–3 and each $R^{13}$ group is independently selected from hydrogen or alkyl; $R^9$ is hydrogen, alkyl, or optionally substituted aryl, or a group $COR^{14}$ where $R^{14}$ is alkyl, aryl, or haloalkyl; and $R^{10}$ and $R^{11}$ are independently selected from hydrogen or alkyl, particularly $C_{1-4}$ alkyl;

$R^3$ is a group $OR^{15}$, $S(O)_qR^{15}$, $NHCOR^{16}$, $NHSO_2R^{16}$, $(CH_2)_sCOOH$, $(CH_2)_tCONR^{17}R^{18}$, $NR^{17}R^{18}$, $SO_2NR^{17}R^{18}$ or optionally substituted alkenyl, where q is 0, 1 or 2, s is 0 or an integer of from 1 to 4, t is 0 or an integer of from 1 to 4, $R^{15}$ is a cycloalkyl group or an alkyl group substituted with one or more groups selected from halogen, hydroxy, cyano, amino, mono- or di-alkylamino, $C_{1-4}$ alkoxy, carboxy, sulphonamido, $CONH_2$, morpholino, pyridinyl, pyrimidinyl, phenyl optionally substituted by halogen, carboxy, alkoxy, carbamoyl, acyl groups, or hydroxyalkyl wherein the alkyl group in the hydroxyalkyl moiety includes at least two carbon atoms $R^{16}$ is optionally substituted alkyl or optionally substituted aryl, and $R^{17}$ and $R^{18}$ are independently selected from hydrogen, optionally substituted alkyl, and optionally substituted aryl, with the proviso that at least one of $R^{17}$ or $R^{18}$ is other than hydrogen; and $R^4$ is selected from hydrogen, hydroxyl, halo, alkoxy, aryloxy, araalkyl, carboxyalkyl, or an amide derivative thereof; and $R^5$, $R^6$, and $R^7$ are independently selected from hydrogen, hydroxyl, halo, alkoxy, or an optionally substituted hydrocarbyl group, subject to the following provisos:
(i) when $R^2$ is carboxy or a salt or amide thereof, at least three of $R^4$, $R^5$, $R^6$, and $R^7$ are hydrogen, and $R^3$ is $S(O)_qR^{15}$, then $R^{15}$ is other than $C_{1-4}$ alkyl substituted by carboxy or an ester or amide derivative thereof;
(ii) when $R^3$ is a group $NHCOR^{16}$, then $R^{16}$ is optionally substituted alkyl; and
(iii) when $R^3$ is a group $SR^{15}$, where $R^{15}$ is 2-quinolylmethyl, $R^2$ is COOH or an ethyl ester thereof, each of $R^4$, $R^5$, and $R^7$ are hydrogen, and $R^1$ is 4-chlorophenyl, then $R^6$ is other than 2-quinolylmethyl;
(iv) when $R^3$ is a group COOH or $CH_2COOH$, $R^2$ is COOH and each of $R^4$, $R^5$, $R^6$ and $R^7$ are hydrogen, then $R^1$ is other than unsubstituted phenyl;
(v) when $R^3$ is a group $CH_2COOH$, $R^2$ is COOH and each of $R^4$, $R^5$, and $R^7$ are hydrogen, $R^1$ is 4-chlorophenyl, then $R^6$ is other than methoxy;
(vi) when $R^3$ is $OR^{15}$ or $S(O)_qR^{15}$, then $R^{15}$ is other than $C_{1-6}$ haloalkyl; and
(vii) when $R^2$ is $COOCH_2CH_3$, each of $R^4$, $R^5$, $R^6$ and $R^7$ are hydrogen, and $R^1$ is 4-chlorophenyl, then $R^3$ is other than a group $CH=CH(CN)_2$.

8. A method of preparing a compound of formula (I):

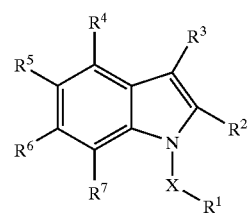

(I)

or a pharmaceutically acceptable salt or ester thereof; wherein

X is $CH_2$ or $SO_2$;

$R^1$ is an optionally substituted aryl ring;

$R^2$ is carboxy, cyano, —C(O)CH$_2$OH, —CONHR$^8$, —SO$_2$NHR$^9$, SO$_3$H, where $R^8$ is selected from hydrogen, alkyl, aryl, cyano, hydroxy, —SO$_2$R$^{12}$ where $R^{12}$ is alkyl, aryl, or haloalkyl, or $R^8$ is a group —(CHR$^{13}$)$_r$—COOH where r is an integer of 1–3 and each $R^{13}$ group is independently selected from hydrogen or alkyl; $R^9$ is hydrogen, alkyl, or optionally substituted aryl, or a group COR$^{14}$ where $R^{14}$ is alkyl, aryl, or haloalkyl; and $R^{10}$ and $R^{11}$ are independently selected from hydrogen or alkyl, particularly C$_{1-4}$ alkyl;

$R^3$ is a group OR$^{15}$, S(O)$_q$R$^{15}$, NHCOR$^{16}$, NHSO$_2$R$^{16}$, (CH$_2$)$_s$COOH, (CH$_2$)$_t$CONR$^{17}$R$^{18}$, NR$^{17}$R$^{18}$, SO$_2$NR$^{17}$R$^{18}$ or optionally substituted alkenyl, where q is 0, 1 or 2, s is 0 or an integer of from 1 to 4, t is 0 or an integer of from 1 to 4, $R^{15}$ is a cycloalkyl group or an alkyl group substituted with one or more groups selected from halogen, hydroxy, cyano, amino, mono- or di-alkylamino, C$_{1-4}$ alkoxy, carboxy, sulphonamido, CONH$_2$, morpholino, pyridinyl, pyrimidinyl, phenyl optionally substituted by halogen, carboxy, alkoxy, carbamoyl, acyl groups, or hydroxyalkyl wherein the alkyl group in the hydroxyalkyl moiety includes at least two carbon atoms, $R^{16}$ is optionally substituted alkyl or optionally substituted aryl, and $R^{17}$ and $R^{18}$ are independently selected from hydrogen, optionally substituted alkyl, and optionally substituted aryl, with the proviso that at least one of $R^{17}$ or $R^{18}$ is other than hydrogen; and $R^4$ is selected from hydrogen, hydroxyl, halo, alkoxy, aryloxy, araalkyl, carboxyalkyl, or an amide derivative thereof; and $R^5$, $R^6$, and $R^7$ are independently selected from hydrogen, hydroxyl, halo, alkoxy, or an optionally substituted hydrocarbyl group, which method comprises reacting a compound of formula (VII)

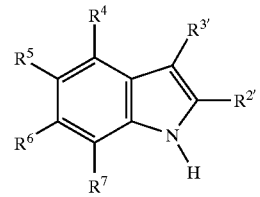

(VII)

$R^{2'}$ is a group $R^2$ or a protected form thereof, and $R^{3'}$ is a group $R^3$; with a compound of formula (VIII)

$$R^1—X—Z^1 \quad \text{(VIII)}$$

where $R^1$ is an optionally substituted aryl ring and X is CH$_2$ or SO$_2$ and Z1 is a leaving group; and thereafter optionally removing any protecting group from R2'.

* * * * *

UNITED STATES PATENT AND TRADEMARK OFFICE
CERTIFICATE OF CORRECTION

PATENT NO. : 6,833,387 B1
DATED : December 21, 2004
INVENTOR(S) : Faull et al.

It is certified that error appears in the above-identified patent and that said Letters Patent is hereby corrected as shown below:

Column 4,
Line 6, after "Alkoxy, or" insert -- aryloxy. --;

Column 25,
Formula (XIII), delete "$R^{3'}$" and instead insert -- $R^{3''}$ --;
Formula (XIV), delete "$R^{3''''}$" and instead insert -- $R^{3''}$ --;

Column 29,
Line 58, delete "$MH^{30}$" and instead insert -- $MH^+$ --;

Column 30,
Line 59, delete "$MH^{30}$" and instead insert -- $MH^+$ --;

Column 31,
Line 24, delete the second instance of "in";

Column 33,
Line 15, delete "571" and instead insert -- 5.71 --;

Column 35,
Line 5, before "7.12" insert -- 6.96(dd, 1H), --;
Line 42, before "321" insert -- 323 --;

Column 37,
Line 45, delete "$MH^{30}$" and instead insert -- $MH^+$ --;

Column 40,
Line 10, delete "(3 mg)" and instead insert -- (300) --;

Column 45,
Line 38, delete "LIOH" and instead insert -- LiOH --;

Column 46,
Line 3, delete "7.2" and instead insert -- 7.27 --;
Line 4, delete the first instance of "7";
Line 47, delete "," and instead insert -- . --;
Line 58, delete "ixo" and instead insert -- iso --;

Column 48,
Line 48, delete "$NA_2HPO_4$" and instead insert -- $Na_2HPO_4$ --;

UNITED STATES PATENT AND TRADEMARK OFFICE
CERTIFICATE OF CORRECTION

PATENT NO. : 6,833,387 B1
DATED : December 21, 2004
INVENTOR(S) : Faull et al.

It is certified that error appears in the above-identified patent and that said Letters Patent is hereby corrected as shown below:

Column 50,
Line 41, delete "$[Ca^{2+}]_i$" and instead insert -- $[Ca^{2+}]i$ --; and
Line 62, delete "Md." and instead insert -- MD --.

Signed and Sealed this

Twenty-seventh Day of September, 2005

JON W. DUDAS
*Director of the United States Patent and Trademark Office*